(12) United States Patent
Albert et al.

(10) Patent No.: US 11,850,356 B1
(45) Date of Patent: Dec. 26, 2023

(54) APPARATUS, METHODS, AND SYSTEMS FOR ADMINISTERING A MEDICATION TO A PATIENT FROM A CAPSULE USING AN ATOMIZER

(71) Applicant: MICRONEB TECH HOLDINGS, INC., St Petersburg, FL (US)

(72) Inventors: Pradeep Albert, Sarasota, FL (US); Christine Nichols, Largo, FL (US); David J. Condron, Seminole, FL (US); Brian Artze, Gulfport, FL (US); Fadi Saba, St Petersburg, FL (US); Jesse Klein, Clearwater, FL (US); Vijay Vad, New York, NY (US)

( * ) Notice: Subject to any disclaimer, the term of this patent is extended or adjusted under 35 U.S.C. 154(b) by 0 days.

(21) Appl. No.: 18/207,242

(22) Filed: Jun. 8, 2023

(51) Int. Cl.
| | |
|---|---|
| *A61M 15/00* | (2006.01) |
| *A61M 16/06* | (2006.01) |
| *A61M 16/00* | (2006.01) |
| *A61M 11/00* | (2006.01) |

(52) U.S. Cl.
CPC ...... *A61M 15/0086* (2013.01); *A61M 11/005* (2013.01); *A61M 15/0016* (2014.02); *A61M 16/0084* (2014.02); *A61M 16/0622* (2014.02); *A61M 2210/0618* (2013.01)

(58) Field of Classification Search
CPC .......... A61M 15/0085; A61M 15/0086; A61M 16/0078; A61M 16/0084; A61M 11/005
See application file for complete search history.

(56) References Cited

U.S. PATENT DOCUMENTS

| | | | | |
|---|---|---|---|---|
| 5,988,162 A | * | 11/1999 | Retallick, III | .... A61M 16/0084 128/200.14 |
| 5,996,579 A | * | 12/1999 | Coates | .............. A61M 16/0084 128/205.13 |
| 6,276,363 B1 | * | 8/2001 | Gray | ................. A61M 16/0463 128/205.24 |

(Continued)

FOREIGN PATENT DOCUMENTS

| | | |
|---|---|---|
| CN | 112535782 A1 | 3/2021 |
| CN | 106178202 B | 5/2022 |

(Continued)

OTHER PUBLICATIONS

Zoonar, Robert Byron, Inhaler Bag, Alamy, website: https://www.alamy.com/stock-photo-inhaler-bag-82323224.html?imageid=CD92FA2A-D6F1-47CC-9D78-0DB8E7FBDCD1&p=259022&pn=1&searchid=d8cb6bd13b7cbf81bad32d700518330b&searchtype=0.

*Primary Examiner* — Kathryn E Ditmer
(74) *Attorney, Agent, or Firm* — Derek Fahey, Esq.; The Plus IP Firm, PLLC

(57) ABSTRACT

A system for administering at least one medication to a patient is disclosed. The system includes a resilient air bladder in fluid communication with a tubular chamber of a base unit, a capsule in fluid communication with the tubular chamber configured for carrying the at least one medication, and an atomizer disposed at least proximate to the capsule and in fluid communication with the tubular chamber. An air inlet and a first one-way valve is in fluid communication with the resilient air bladder configured to allow fresh air to (Continued)

enter the resilient air bladder. An air outlet and a second one-way value is in fluid communication the resilient air bladder and the tubular chamber. Fresh air and the medication atomized by the atomizer mix together within the tubular chamber.

19 Claims, 21 Drawing Sheets

(56) References Cited

U.S. PATENT DOCUMENTS

| | | | |
|---|---|---|---|
| 6,792,947 B1 * | 9/2004 | Bowden | A61M 16/0866 128/207.14 |
| 6,978,779 B2 * | 12/2005 | Haveri | A61M 16/147 128/204.22 |
| 7,207,329 B2 * | 4/2007 | Bowden | A61M 16/08 128/203.12 |
| 11,040,156 B2 | 6/2021 | Riebe et al. | |
| 11,285,285 B2 * | 3/2022 | Germinario | A61M 15/0091 |
| 2003/0150445 A1 * | 8/2003 | Power | A61M 16/049 128/200.14 |
| 2004/0094150 A1 * | 5/2004 | Flynn | A61M 16/0057 128/202.28 |
| 2008/0142010 A1 * | 6/2008 | Weaver | A61M 11/001 128/203.29 |
| 2008/0271732 A1 * | 11/2008 | Weaver | A61M 15/025 128/200.14 |
| 2009/0134235 A1 * | 5/2009 | Ivri | A61M 15/0085 29/25.35 |
| 2010/0044460 A1 * | 2/2010 | Sauzade | A61M 15/0085 239/102.2 |
| 2010/0180890 A1 | 6/2010 | Nobutani | |
| 2010/0326436 A1 | 12/2010 | Kaneko | |
| 2011/0108025 A1 * | 5/2011 | Fink | A61M 15/0085 128/200.23 |
| 2011/0277754 A1 * | 11/2011 | Mckinnon | A61M 16/0084 128/203.12 |
| 2011/0283996 A1 | 11/2011 | Abrams | |
| 2012/0266878 A1 | 10/2012 | Watanabe | |
| 2013/0119151 A1 * | 5/2013 | Moran | A61M 11/005 239/102.2 |
| 2014/0116426 A1 | 5/2014 | Mullinger et al. | |
| 2014/0230821 A1 * | 8/2014 | Warters | A61M 16/06 128/206.28 |
| 2016/0339198 A1 * | 11/2016 | Fraser | A61K 31/485 |
| 2017/0203055 A1 * | 7/2017 | Chen | B05B 17/0646 |
| 2017/0304565 A1 * | 10/2017 | Allosery | A61K 39/42 |
| 2018/0110941 A1 | 4/2018 | Smith | |
| 2018/0214636 A1 | 8/2018 | Amirouche | |
| 2019/0038854 A1 * | 2/2019 | Fuchs | A61M 15/00 |
| 2020/0187565 A1 * | 6/2020 | Williams | A61M 11/005 |
| 2020/0306466 A1 * | 10/2020 | Pell | B05B 17/0646 |
| 2020/0360005 A1 | 11/2020 | Rodriguez Salazar et al. | |
| 2020/0368457 A1 | 11/2020 | Clark et al. | |
| 2020/0390984 A1 * | 12/2020 | Hua | A61M 11/00 |
| 2021/0077753 A1 | 3/2021 | Pell et al. | |
| 2021/0252231 A1 * | 8/2021 | Casey | B05B 17/0646 |
| 2021/0260312 A1 | 8/2021 | Lacour-Gayet et al. | |
| 2021/0346613 A1 | 11/2021 | Khaitan | |
| 2022/0040418 A1 * | 2/2022 | Blick | B05B 17/0646 |
| 2022/0226587 A1 * | 7/2022 | Hunter | A61M 15/0021 |
| 2022/0273235 A1 | 9/2022 | Markey et al. | |

FOREIGN PATENT DOCUMENTS

| | | | | |
|---|---|---|---|---|
| EP | 2537548 A2 | * | 12/2012 | A61M 11/005 |
| GB | 2285396 A | * | 7/1995 | A61M 15/0086 |
| GB | 2442267 A | * | 4/2008 | A61M 16/0078 |
| JP | 2004505730 A | | 2/2004 | |
| JP | 2019515684 A | | 6/2019 | |
| JP | 2020518336 A | | 6/2020 | |
| JP | 2022537164 A | | 8/2022 | |
| WO | WO2022034036 A1 | | 2/2022 | |
| WO | WO-2022185271 A2 | * | 9/2022 | |
| WO | WO-2022192736 A1 | * | 9/2022 | |
| WO | WO2022192736 A1 | | 9/2022 | |

* cited by examiner

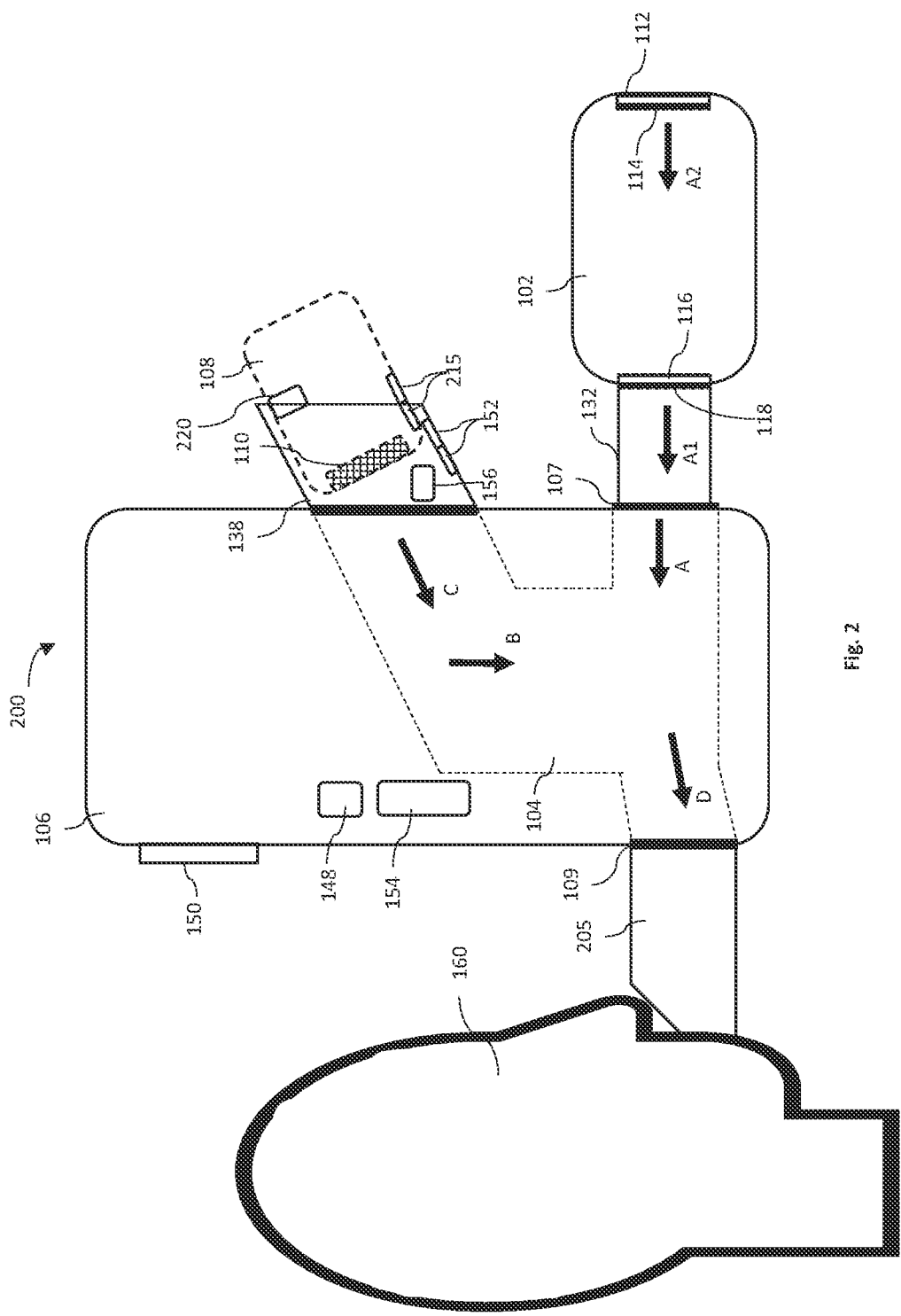

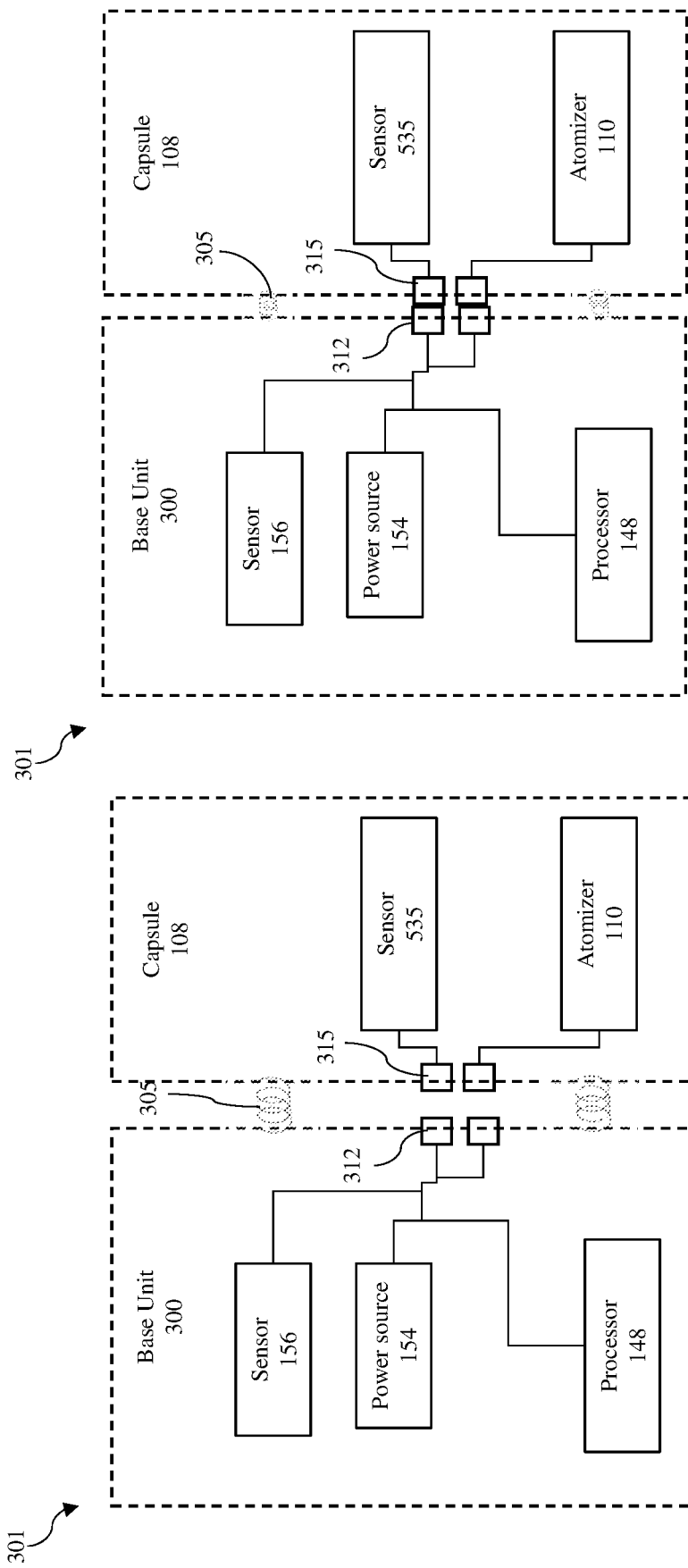

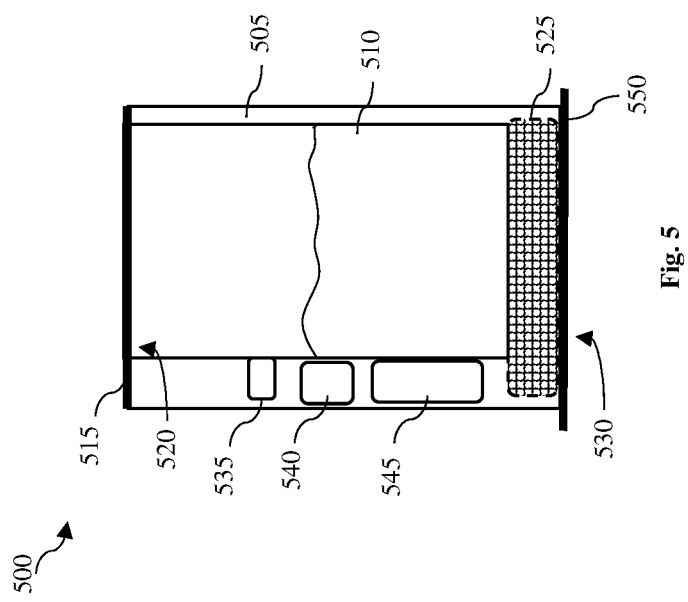

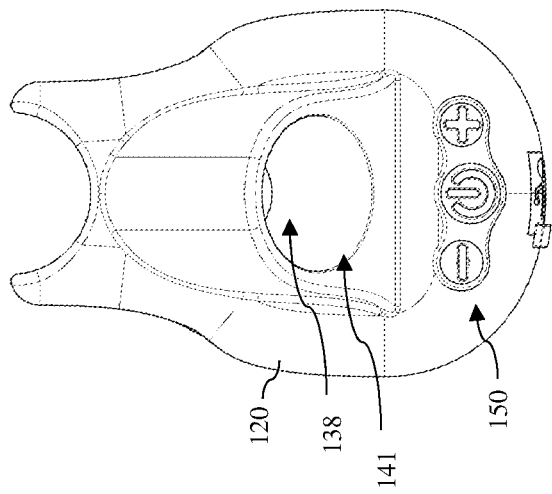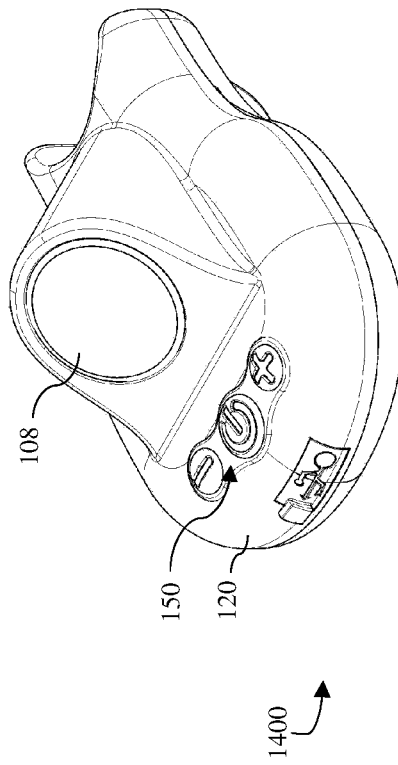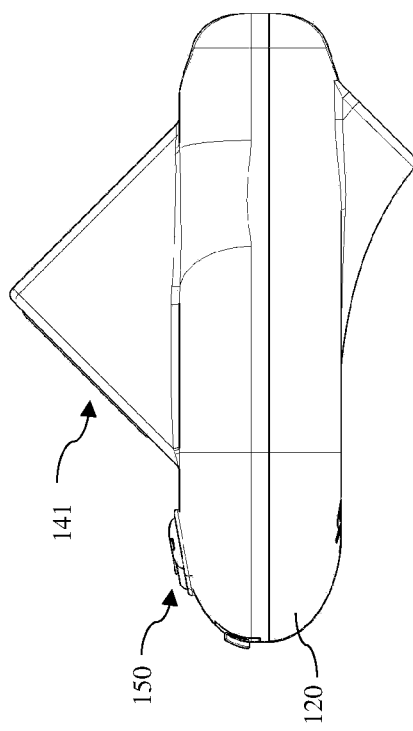
FIG. 14B
FIG. 14A
FIG. 14C

APPARATUS, METHODS, AND SYSTEMS FOR ADMINISTERING A MEDICATION TO A PATIENT FROM A CAPSULE USING AN ATOMIZER

REFERENCE TO RELATED APPLICATIONS

Not applicable.

CROSS-REFERENCES

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

TECHNICAL FIELD

The present disclosure relates to the field of mesh nebulizers, and more specifically to the field of mesh nebulizers for administering medications.

BACKGROUND OF THE INVENTION

A mesh nebulizer, also known as a vibrating mesh nebulizer, is a type of device used to deliver medication in a fine mist or aerosol form, which makes it easier for patients to inhale the medication directly into their lungs. This is particularly useful for the treatment of respiratory diseases like asthma, COPD (chronic obstructive pulmonary disease), or cystic fibrosis. The "mesh" in the name refers to a key component of the nebulizer: a small plate with multiple tiny holes, or a "mesh". This mesh vibrates at high frequencies, causing the liquid medication to be pushed through the tiny holes in the mesh, creating a fine mist or aerosol that can be inhaled. Mesh nebulizers are generally more efficient and portable than traditional jet nebulizers. They tend to be quiet, lightweight, and capable of nebulizing a wide range of medications. However, they can be more expensive, and the mesh plate can become blocked over time, requiring replacement. Proper cleaning and maintenance are important to keep the device functioning properly.

Inhalers are devices used to deliver medication directly into the lungs. They are commonly used to treat conditions like asthma and chronic obstructive pulmonary disease (COPD). There are two main types of inhalers: metered-dose inhalers (MDIs) and dry powder inhalers (DPIs). MDIs use a chemical propellant to push the medication out of the inhaler. The user pushes down on the top of the inhaler and inhales at the same time to ensure the medication reaches the lungs. MDIs also can be used with a spacer, a tube-like device which provides a space for the medication to mix with air before reaching the lungs. This makes it easier for the medication to be inhaled and is especially helpful for children or people who have difficulty coordinating their breath with the release of the medication. DPIs do not use a chemical propellant. Instead, the medication is in a powder form, which the user inhales. Because they require a strong, quick inhalation to get the medication into the lungs, DPIs can be harder for some people to use than MDIs. Inhalers can deliver a variety of medications. However, the effectiveness of inhalers depends significantly on correct usage. Mistakes in technique can result in less medication reaching the lungs. These mistakes could include breathing too quickly or not deeply enough, not shaking the inhaler before use, or not using a spacer if needed. Some inhalers, especially newer or brand-name inhalers, can be quite expensive, potentially posing a financial burden.

As a result, there exists a need for improvements over the prior art and more particularly for a more efficient way of administering medication to a patient.

BRIEF SUMMARY OF THE INVENTION

An apparatus, method, and system for administering at least one medication to a patient is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a method of administering at least one medication to a patient into the patient's mouth is disclosed. The method includes dispensing, using an atomizer, the at least one medication from a capsule in fluid communication with a tubular chamber, into the tubular chamber; and causing, air within a resilient air bladder in fluid communication with the tubular chamber to be conveyed from the resilient air bladder and into the tubular chamber such that the air conveyed from the resilient air bladder and the at least one medication dispensed from the capsule is administered to the patient. The method also includes, prior to dispensing the at least one medication from the capsule, disposing a device on the patient's face and or a mouthpiece defining a tubular shaped body to be inserted into the patient's mouth. The device includes a mask defining a mask chamber within the mask that is surround by a rim on the periphery of the mask. The mask is to be positioned over the patient's mouth and nose, and by applying force with a hand of a rescuer to the mask to obtain a substantially air-tight seal against the patient's face. While applying the force with the hand of the rescuer to the mask, engaging with a second hand of the rescuer, a user interface on the device to cause the atomizer to atomize and to dispense the at least one medication from the capsule. While applying the force to the mask with the hand of the rescuer, and either during or after engaging with the user interface to cause the dispensing of the at least one medication from the capsule, the method further includes applying a second force with the second hand of the rescuer, to the resilient air bladder so that the air within the resilient air bladder is conveyed from the resilient air bladder and into the tubular chamber such that the air conveyed from the resilient air bladder and the at least one medication dispensed from the capsule is administered to the patient. One inventive aspect of this device is that only a single rescuer may be needed to easily administer medication to a patient.

Prior to dispensing the at least one medication from the capsule, the method further includes receiving, with a processor, a signal to start the atomizer to atomize the at least one medication, determining, using the processor based on the signal, a maximum volume of the at least one medication to atomize and/or a maximum amount of time to atomize the at least one medication. Next, the process sends, to the atomizer, a signal to cause the atomizer to atomize the maximum volume of the at least one medication and/or the at least one medication for the maximum amount of time. After the maximum volume or time has been attained, the process the receives, a third signal from a sensor that monitors an atomized volume of the at least one medication within the capsule or a first amount of time the atomizer atomizes the at least one medication. The signal is received from at least one of a remote computing device and the capsule. The method includes, after the processor determines that the atomized volume is at least as much as the maximum volume based on the third signal received and/or the first amount of time is at least as much as the maximum amount of time, then stopping the atomizer from continuing to atomize the at least one medication within the capsule. The processor is configured to send a fourth signal to stop the atomizer from continuing to atomize the at least one medication within the capsule after the processor determines that the atomized volume is at least as much as the maximum volume based on the third signal received.

In another embodiment, a system for administering at least one medication to a patient is disclosed. The system includes a resilient air bladder in fluid communication with a tubular chamber of a base unit, a capsule in fluid communication with the tubular chamber configured for carrying the at least one medication, and an atomizer disposed at least proximate to the capsule and in fluid communication with the tubular chamber. The atomizer is configured to atomize the at least one medication that is disposed within the capsule. The system further includes an air inlet and a first one-way valve in fluid communication with the resilient air bladder configured to allow fresh air to enter the resilient air bladder. The system includes an air outlet and a second one-way value in fluid communication the resilient air bladder and the tubular chamber. Fresh air is drawn into the resilient air bladder when it inflates.

Fresh air is forced through the second one-way valve and to the tubular chamber when the resilient air bladder deflates. Fresh air and the at least one medication atomized by the atomizer to mix together within the tubular chamber. The system further includes a mask defining a mask chamber within the mask. The mask is positioned over the patient's mouth and nose, a rim extending about a periphery of the mask for forming a seal with the patient's face. In another embodiment, the system may include a mouthpiece defining a tubular shaped body. The capsule includes a capsule chamber for housing the at least one medication, a rubber section covering an open side of the capsule, the atomizer proximate to a second side of the capsule, and a sensor for detecting an amount of the at least one medication in the capsule.

The system further includes a housing and a first channel spanning from a first side of the housing to a second side of the housing. The system further includes a first longitudinal axis of the first channel, a first end portion of the first channel configured to receive a portion of a conduit that is in fluid communication with the air outlet of the resilient air bladder, and a second end portion of the first channel configured to receive a portion of either the mouthpiece or the mask. The system further includes a second channel disposed on the housing configured to receive a portion of the capsule and a second longitudinal axis defined by the second channel. The second longitudinal axis defines at most a 90-degree angle relative to the first longitudinal axis of the first channel. However, other angles, such as a 45-degree angle may be used and is within the spirit and scope of the present invention.

The system further includes a processor housed by the housing. The housing houses the user interface housed by the housing. The user interface is configured to be acted on by a rescuer to start the atomizer to atomize the at least one medication. The user interface, may include control for being manipulated by the hands of a user, a graphical display, an audio sensor for receiving audio signals from the user to control the device. The processor is configured for receiving a signal to start the atomizer to atomize the at least one medication, sending a second signal to the atomizer to cause the atomizer to atomize the at least one medication within the capsule and convey the atomized at least one medication into the second channel, receiving a third signal from the sensor when the sensor detects that the at least one medication within the capsule is less than a minimum threshold, and sending a fourth signal to turn off the atomizer after the third signal is received.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 1 is a diagram of a side view of a system for administering medication to a patient, according to a first embodiment;

FIG. 1A is a diagram of a side view of a system for administering medication to a patient, wherein the resilient air bladder is deflated by the force of a rescuer, according to a first embodiment;

FIG. 1B is a diagram of a side view of an attachment for administering medication to a patient, according to a first embodiment;

FIG. 2 is a diagram of a side view of a system for administering medication to a patient, according to a second embodiment;

FIG. 3A is a diagram of a side view of a system for administering medication to a patient, according to a third embodiment, wherein a biasing element is in an extended state;

FIG. 3B is a diagram of a side view of a system for administering medication to a patient, according to the third embodiment, wherein a biasing element is in a compressed state;

FIG. 3C is a diagram illustrating the main electrical components of the system for administering medication to a patient, wherein biasing elements are in an extended state, according to the third embodiment;

FIG. 3D is a diagram illustrating the main electrical components of the system for administering medication to a patient, wherein biasing elements are in a compressed state, according to the third embodiment;

FIG. 4 is a diagram illustrating the main electrical components of a system for administering medication to a patient, according to an example embodiment;

FIG. 5 is a diagram of a front view of a capsule, according to an example embodiment;

FIG. 14A is a perspective view of an attachment for administering medication to a patient, according to the first embodiment;

FIG. 14B is a top view of an attachment for administering medication to a patient, according to the first embodiment;

FIG. 14C is a side view of an attachment for administering medication to a patient, according to the first embodiment;

Like reference numerals refer to like parts throughout the various views of the drawings. FIGS. 11A through 16B are drawn to scale.

DETAILED DESCRIPTION

Figure 1:
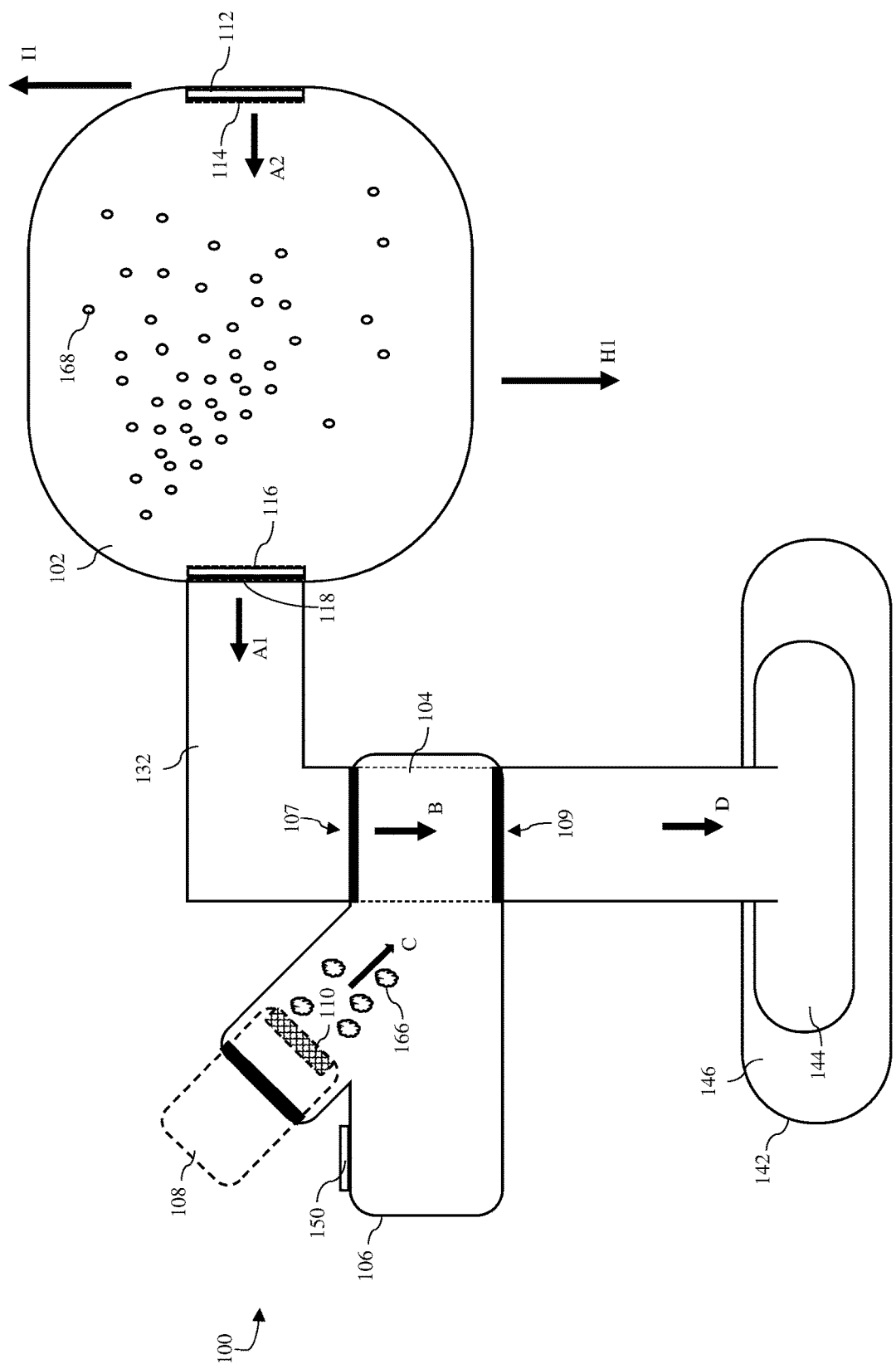

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing an apparatus, system, and method that allows for controlled and measured doses of medication that need to be administered to a patient via inhalation, such as in the treatment of respiratory conditions or overdoses. The method allows for precise administration of the medication because it ensures the system administers the medication in the capsule depending on the needs of certain medical situations. The system includes modular components such that the apparatus can be utilized in different scenarios. For example, depending on the type of modular cardiopulmonary device, the system may be used on a patient that is laying down, positioned upright, conscious, or unconscious. The system may allow a patient to treat themselves or may require an authorized user to treat the patient using the system. The system is configured to only require one rescuer having two hands to operate the system.

Additionally, the system is more convenient than the prior art because the attachment for the modular cardiopulmonary device includes integrated medication monitoring and an adjustably automated dispensing of medication. The attachment also allows for more adaptability and portability because it has modular fittings that can allow for attachment with commonly used cardiopulmonary devices, such as resuscitation bags and breathing masks.

The system also improves over the prior art because the medication is held in capsules that includes an atomizer that abuts the medication. Gravity forces the medication to be pressed against the medication to allow for efficient atomization. The capsule is compatible with the attachment because both include electrical contacts that, when paired up, provide electrical communication between the capsule and the attachment.

Figure 1A:
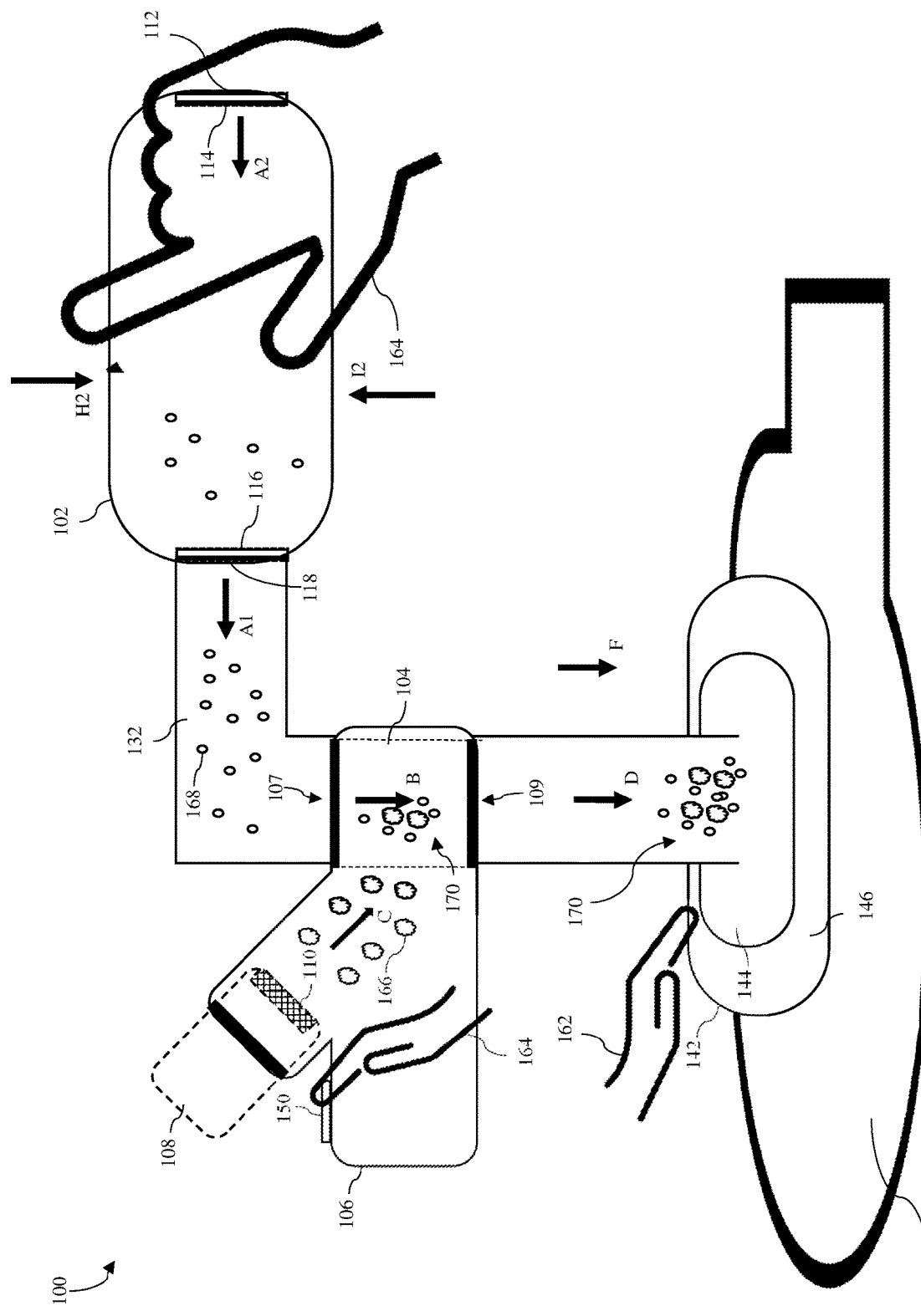
Figure 1B:
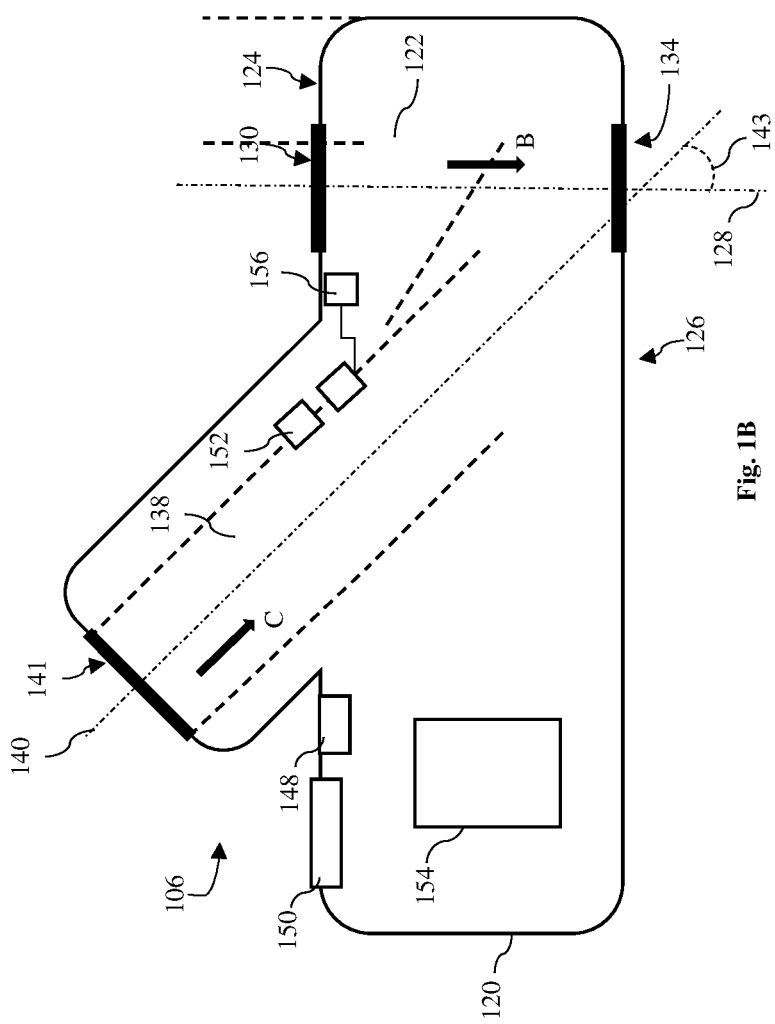
Figure 13:
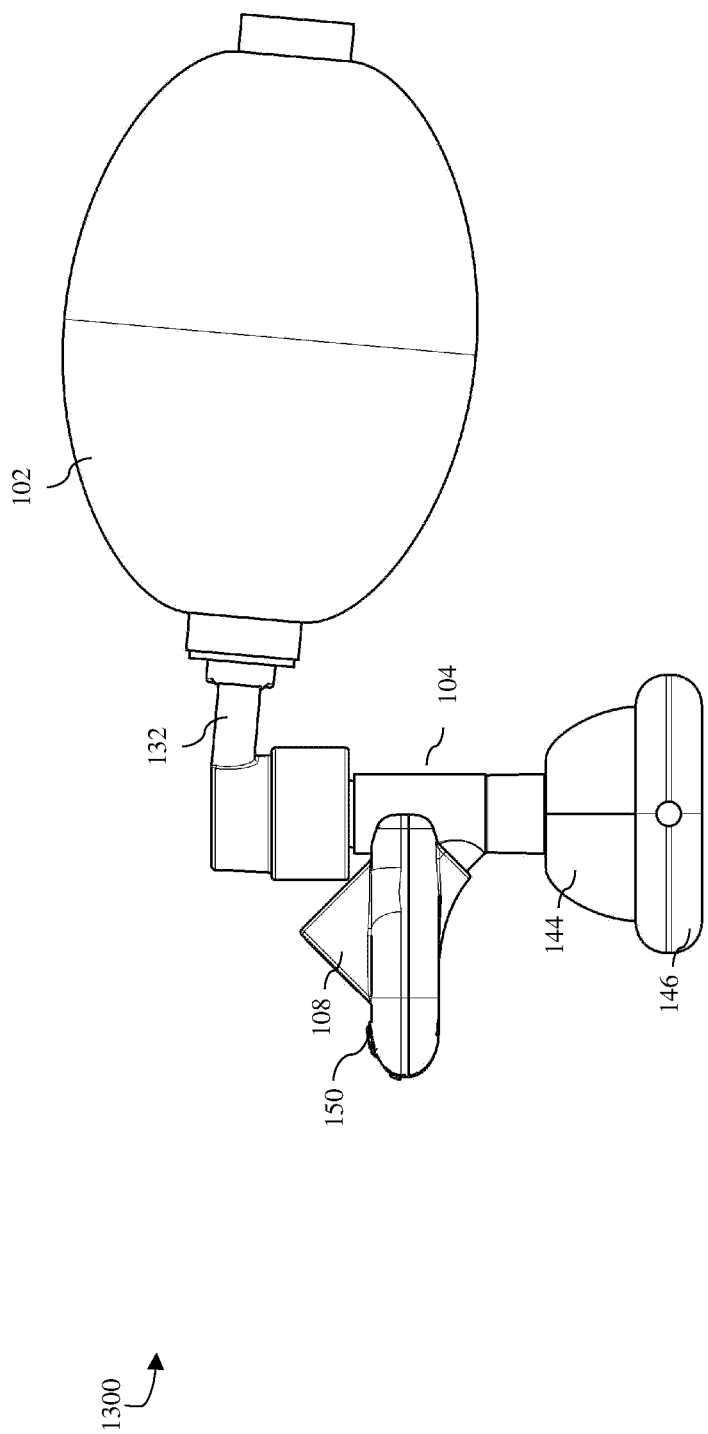
FIG. 13 is a side view of a system for administering medication to a patient, according to the first embodiment.
Figure 15A:
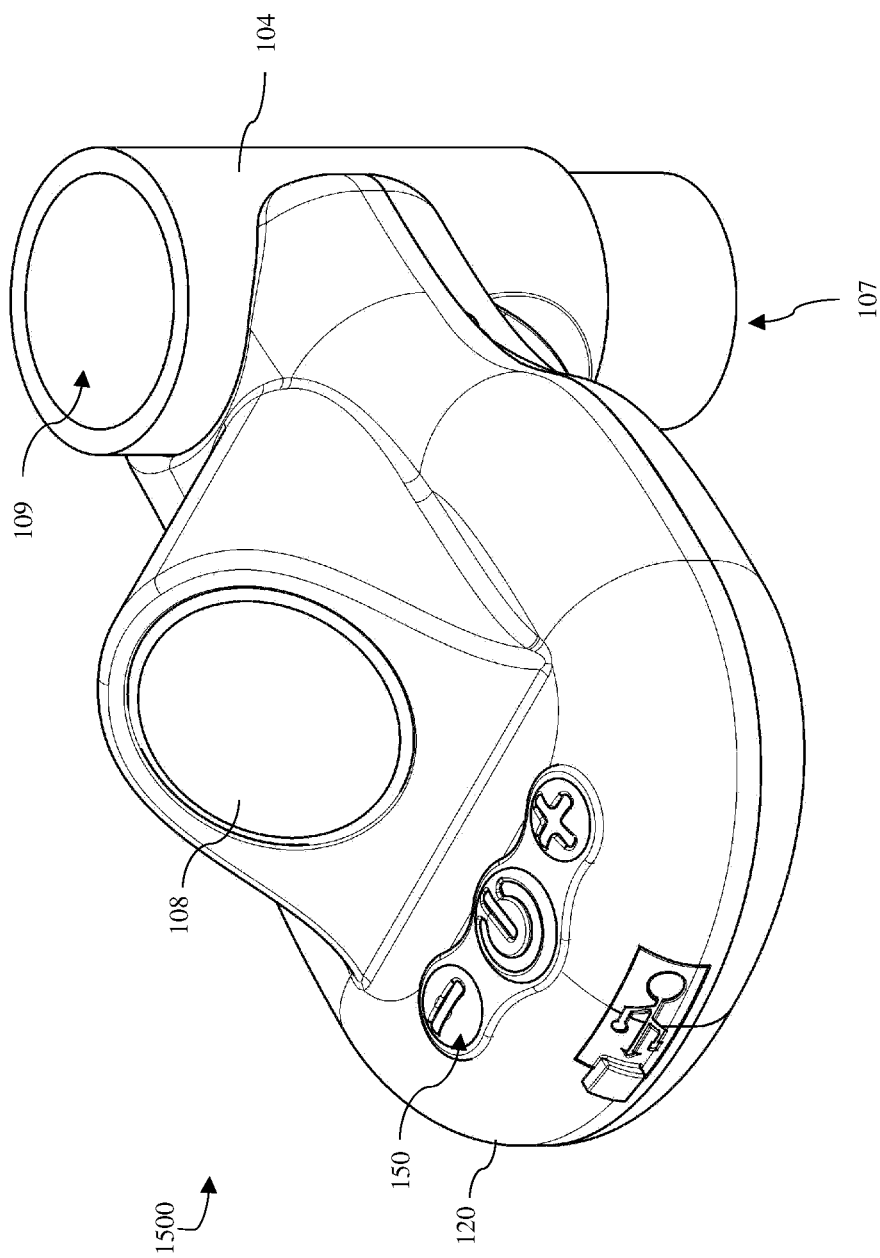
FIG. 15A is a perspective view of an attachment for administering medication to a patient, according to the first embodiment.
Figure 15B:
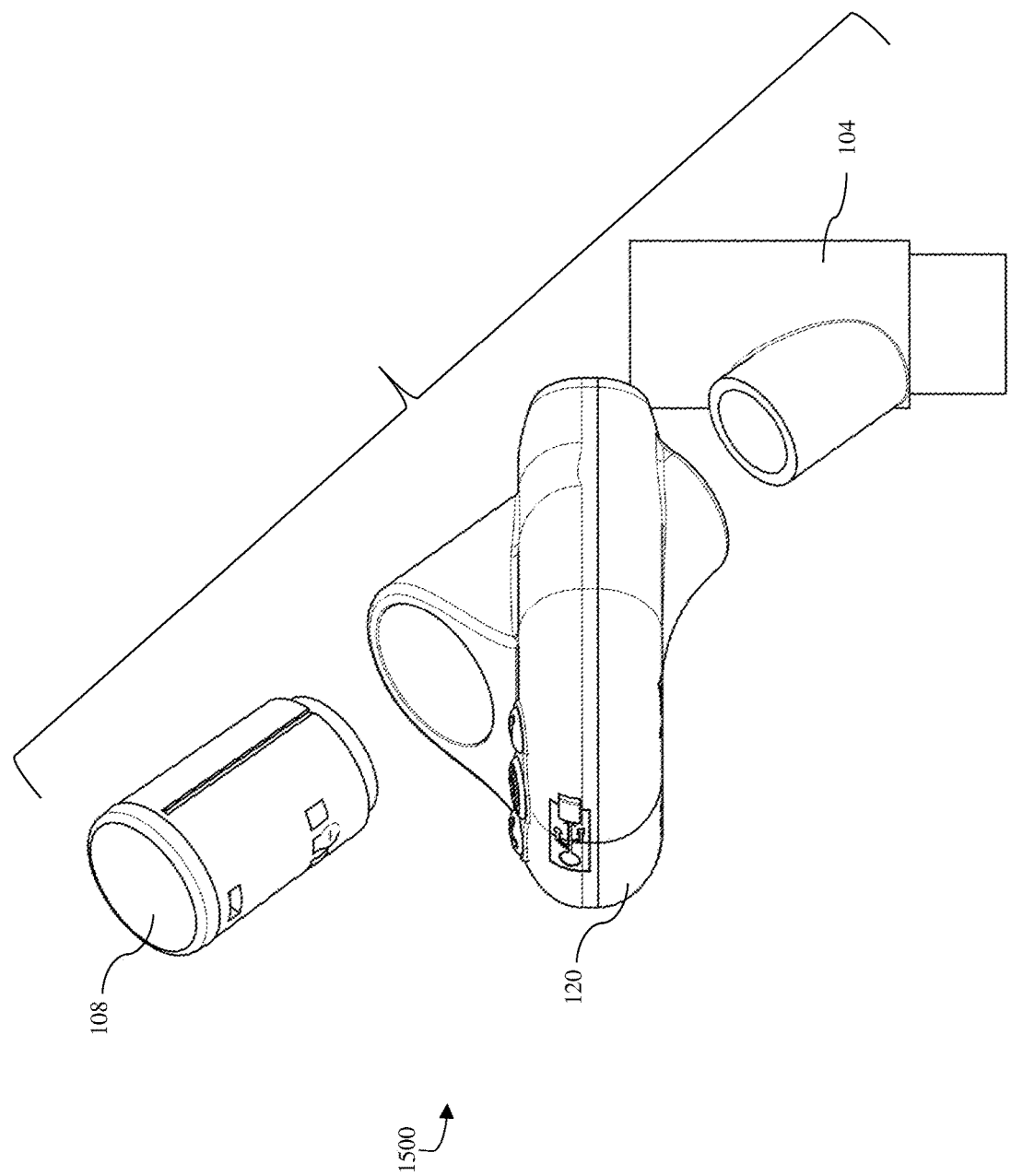
FIG. 15B is an exploded perspective view of an attachment for administering medication to a patient, according to the first embodiment.
Figure 16B:
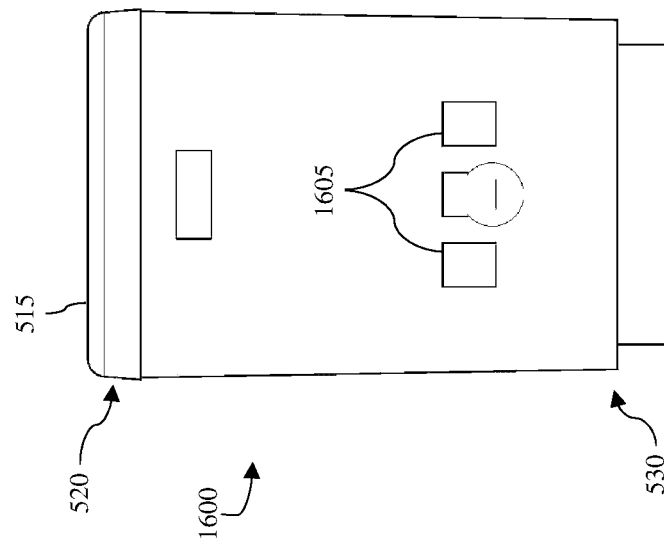
FIG. 16B is a front view of the capsule, according to an example embodiment.
Figure 16A:
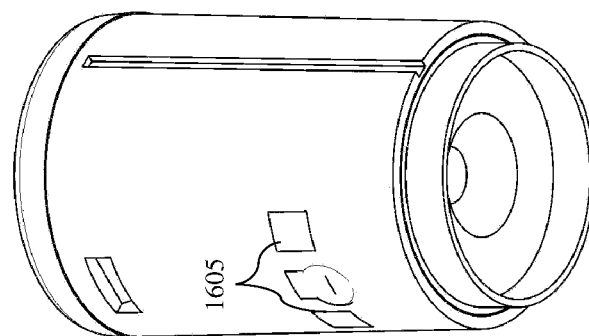
FIG. 16A is a bottom perspective view of the capsule, according to an example embodiment.

Referring now to the Figures, FIG. 1A is a side view of a system 100 for administering at least one medication to a patient, according to a first embodiment. FIG. 1B is a side view of a base unit or an attachment 106 for administering medication to a patient, according to the first embodiment. Additionally, FIGS. 13 through 15B also depict views of another example of the first embodiment. FIG. 13 is a side view of the system 1300, according to the first embodiment. FIGS. 14A through 14C are various views of the housing of the system 1400, according to the first embodiment. FIG. 15A is a perspective view of the attachment 1500, according to the first embodiment. FIG. 15B is an exploded perspective view of the attachment 1500, according to the first embodiment. The medication is in fluid form. The system includes a resilient air bladder 102 in fluid communication with a tubular chamber 104 of a base unit. The tubular chamber is a hollow enclosed space within the base unit. The resilient air bladder supplies the system with fresh air. Other types of cardiopulmonary devices configured to supply air into the system may be used and are within the spirit and scope of the present invention. The resilient air bladder is a resuscitation bag, which is commonly used by medical professionals.

The base unit is the attachment 106 that including receiving sections 107 and 109 that provides modular fittings such that commonly used medical components, such as medical face masks or medical mouthpieces, and modular cardiopulmonary devices may be attached. Each of the receiving sections includes an opening into the first channel. The first channel may have a cross-sectional shape defining a circle, but other shapes may be used and are within the spirit and scope of the present invention and as such the openings of the receiving sections 107 and 109 may also be a circular shaped opening. The attachment is configured for connecting to a modular cardiopulmonary device. The modular cardiopulmonary device is defined by the resilient air bladder and at least a mask 142 or mouthpiece (205 in FIG. 2). Modular fittings refer to pre-manufactured parts or components that can be assembled, interchanged, or replaced with relative ease. They are designed to be used in different configurations to meet various requirements. The key advantage of modular fittings is their versatility and ease of use, as they allow for customization and flexibility. Modular fittings provide a standardized, interchangeable set of parts that can be used in a variety of configurations to meet different needs. Examples of modular fittings may include, but are not limited to, friction fit, male female fit, or screw fit. Other types of modular fittings configured to allow the attachment 106 to attach to modular cardiopulmonary devices may be included and are within the spirit and scope of the present invention. The modular fittings allow the user of the system to remove or attach different cardiopulmonary devices so that the user can clean and disinfect the devices between each patient.

A capsule 108 is in fluid communication with the tubular chamber and is configured for carrying the medication. In some embodiments, the capsule may include a sensor (220 in FIG. 2) for detecting the amount of medication within the capsule. An atomizer 110 is disposed at least proximate to the capsule and in fluid communication with the tubular chamber. The atomizer is configured to atomize the medication that is disposed within the capsule. The atomizer is configured to produce particles having a particle diameter ranging from about 1.5 micrometers (μm, or microns) to about 6 micrometers. The atomizer includes a vibrating mesh membrane. As the medication passes through the vibrating mesh membrane, the membrane nebulizes the medication to create a nebulized medication that includes a plurality of particles. The vibrating mesh membrane produces nebulized medication by vibrating at high frequency to trigger particle, or droplet, formation from the medication solution against an inner surface of the membrane on an outer surface of the membrane. The vibrating mesh membrane is a metal piece or plate having a plurality of openings extending through the piece, such that the metal piece, when electrically stimulated to undergo piezoelectric vibration, oscillates against the medication in the capsule 108, causing some of the medication to move through the openings and form small particles on or above the outer surface of the active mesh. The vibrating mesh membrane vibrates at between about 150 kHz and about 300 kHz upon electrical stimulation by an AC|DC current directed to the vibrating mesh membrane. However, other frequencies may be used and are within the spirit and scope of the present invention. The vibrating mesh membrane includes material such as pure titanium, platinum, or palladium, or alloys thereof or the like, or laminated layers of titanium, platinum, or palladium or the like, to produce a piezoelectric effect that results in mesh vibration and particle formation over the outer surface of the mesh in the mouthpiece interior volume. Piezoelectricity is the ability of a material to develop electric charge in response to applied mechanical stress.

The atomizer produces particles that are atomized droplets of the medication. Particles that are larger than 5 micrometers are unable to penetrate into the alveoli of the lungs and are thus of reduced efficiency in being rapidly absorbed by the circulatory system and/or body tissues. The ability of particles to penetrate into the lungs and be absorbed by the depends on the size of the particles. Inhalable particles, ranging in size from 1.5 micrometers to about 6 micrometers, penetrate into the lungs as far as the bronchi because the cilia of the lungs filter the inhalable particles from further travel into the lung volume. Particles ranging in size from 1.5 micrometers to about 5 micrometers are able to penetrate into the alveoli in the lungs and are readily absorbed through the alveoli into the circulatory system and body tissues.

The medication in the capsule is a fluid solution configured to treat patients for different situations. The solution includes an aqueous solution that includes an active ingredient and sodium chloride. The active ingredient includes at least one of nicotine, caffeine, a plurality of vitamins, kratom, Vitamin B12, cotinine, adalimumab, cannabidiol ("CBD"), tetrahydrocannabinol ("THC"), psilocybin, cannabis, ketamine and any combination thereof. The active ingredient may include exosomes, analgesics, antifungals, Benzodiazepines, Antiarrhythmic agents, anti-aging agents, rapamycin, metformin, calcium channel blockers, antibiotics, anti-inflammatory, anti-gout, alpha-beta-adrenergic agonists, Nitroglycerin, adrenergic bronchodilators, cardiovascular agents, central nervous system stimulants and/or depressants, diabetic agents, diuretics, immunologic agents, gastrointestinal agents, common biologics like Humira, Lantus, Remicade, Enbrel, vaccines, psychotherapeutic agents, opiate partial antagonists, opioids, pulmonary agents, hormonal agents, weight loss agents, vitamins/minerals/supplements, Antihyperlipidemics, PCSK9 Inhibitors, Evolocumab, Alirocumab, Inclisiran, Diuretics, Furosemide, Bumetanide, Torsemide, Beta-2 Adrenergic Agonists, Salmeterol, Long-Acting Beta Agonist, Vilanterol, Formoterol, Anticholinergics, Umeclidinium, Glycopyrrolate, Corticosteroid: Budesonide, Fluticasone, Bronchodilators, Tiotropium, Over-active Bladder Medications, Anticholinergics, Ditropan (oxybutynin), Tolterodine, Darifenacin, Muscarinic Antagonists, Trospium, Fesoterodine, Migraine Therapyies, CGRP Receptor Blockers (gepants and monoclonal antibodies ((mAb)), Ubrelvy, Triptans, Ergots, Antiemetics, antagonists of the serotonin, histamine, muscarinic and neurokinin systems, Selective Serotonin 5-HT3 Antagonists, Zofran (ondansetron), Diabetic and Weight loss agents, GLP-1, Semaglutide, GIP+GLP-1, Mounjaro™ (Tirzepatide), Anticonvulsants, Pulmonary medications, Hormones, Biologics, Regenerative Drugs, all essential drugs and medicine as defined by World Health Organization, Vitamins, Caffeine and energy medications, All emergency medicine medications, integrative therapeutics, peptides, ozone, o2, white curcumin, exosomes, gene therapy vectors, erectile dysfunction medications, such as sildenafil citrate, tadalafil, Cialis®, Viagra®. and future classes of therapeutics. The active ingredient may also include preservatives, such as Sodium benzoate, and/or anti-yeast agents, such as potassium sorbate. Other preservatives for medication may be used and are within the spirit and scope of the present invention.

The solution further includes a buffer and/or stabilizer. The buffer helps stabilize and maintain the pH level of the solution. The active ingredient includes approximately up to 10% of the solution. Sodium chloride includes approximately between 10% to 90% of the solution. The buffer includes approximately between 1% to 5% of the total solution. The solution has a pH of approximately between 4 pH and 7.5 pH. The pH range is critical to decrease the effects that the active ingredient may have on the body when inhaled, e.g., an increased amount of acute toxicity which may be present in unprotonated active ingredients above a certain pH.

In a first example solution, the solution is for at least decreasing withdrawal symptoms of a person addicted to nicotine. Said solution includes cotinine being the active ingredient in the solution including approximately between 0.5% and 8% of the solution and a sugar alcohol including approximately between 0.5% to 3% of the solution. The solution further includes a buffer including ethyl alcohol and citric acid. The ethyl alcohol includes approximately between 0.1% to 3% of the solution, and the citric acid comprising approximately between 0.1% to 3% of the solution. Cotinine helps reduce symptoms of nicotine withdrawal. The sugar alcohol and citric acid act as sweeteners to counter the bitterness of cotinine when inhaled. In another embodiment, the solution of the first embodiment may be mixed with a small dose of nicotine.

In a second example solution, the solution is a pulmonary irrigation solution. The solution includes adalimumab being the active ingredient including approximately between 1% to 10% of the solution and a sugar alcohol including approximately between 0.1% to 1% of the solution. Adalimumab helps treat a variety of diseases by fighting infections or bacteria within the lungs. The solution further includes a stabilizer including polyol including approximately between 0.1% to 5% of the solution and surfactant comprising approximately between 0.1% to 5% of the solution. The solution may also include at least one of preservative (at 0.1% of the solution) and anti-mold and anti-yeast agent at (0.1% of the solution), The polyol is at least one of sucrose, histidine, and succinate. The surfactant is polyetherimide. At least one of the buffer and the stabilizer includes at least one buffer selected from the group consisting of histidine, succinate, phosphate, citrate, acetate, sodium bicarbonate, maleate, and tartrate buffers. The buffer does not include a combination of a citrate buffer and a phosphate buffer. This solution is intended for use in the induction of sputum production where sputum production is indicated, such as with Rheumatoid Arthritis, Ankylosing Spondylitis, ulcerative Colitis, Psoriasis, Psoriatic Arthritis, Cystic Fibrosis patients and Bronchoalveolar lavage procedures.

In a third example solution, the active ingredient is naloxone, also known as NARCAN®. Naloxone rapidly counters and/or reverses the effects of opioids. Naloxone is the standard treatment to counter opioid overdoses. Inhalation of naloxone through a portable AVI could quickly save the life of opioid users who overdose.

In a fourth example solution, the active ingredient is colloidal silver. Colloidal silver is a liquid solution including a plurality of silver particles. Colloidal silver treatment can heal a variety of infections, such as the common cold or respiratory infections.

In a fifth example solution, the active ingredient is glucagon. Glucagon is a hormone that raises blood glucose levels and the concentration of fatty acids in the bloodstream. Glucagon treatment helps people who suffer from hypoglycemia. Hypoglycemia occurs when the blood glucose levels are lower than the standard range.

An air inlet 112 and a first one-way valve 114 is in fluid communication with the resilient air bladder configured to allow fresh air to enter the resilient air bladder. The air inlet incudes an opening on which first one-way valve 114 is mounted. An air outlet 116 and a second one-way value 118 is in fluid communication the resilient air bladder and the tubular chamber. The first one-way valve 114 allows fresh air outside the bladder to move into the air bladder through that valve and prevents air from moving out of the first one-way valve 114 when the first one-way valve moves between the deflated state to the fully inflated state.

Fresh air is forced in direction A1 through the second one-way valve and to the tubular chamber when the resilient air bladder deflates. The second one-way valve may be a check valve. The air bladder deflates when opposing forces in directions H2 and I2 are applied via squeezing the air bladder. When the resilient air bladder deflates, fresh air is expelled out of the air outlet 116 in direction A1, and the first one-way valve 114 prevents air from being pushed out from the resilient air bladder through the air inlet. Because the resilient air bladder must return to its original shape, the air bladder automatically inflates in directions H1 and I1 when the forces stop squeezing it. Shown in FIG. 1, when the resilient air bladder inflates, fresh air enters through the air inlet 112 in direction A2 and is drawn into the resilient air bladder, and the second one-way valve 118 prevents air from within the tubular chamber from entering the resilient air bladder thereby not causing air to be potentially sucked from a patient.

The base unit further includes a housing 120 and a first channel 122 spanning from a first side 124 of the housing to a second side 126 of the housing. The housing may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The housing may be made of other materials and is within the spirit and the disclosure. The housing may be formed from a single piece or from several individual pieces joined or coupled together. The components of the housing may be manufactured from a variety of different processes including an extrusion process, a mold, casting, welding, shearing, punching, folding, 3D printing, CNC machining, etc. However, other types of processes may also be used and are within the spirit and scope of the present invention.

The system further includes a first longitudinal axis 128 of the first channel. A first end portion 130 of the first channel is configured to receive a portion of a conduit 132 that is in fluid communication with the air outlet of the resilient air bladder, and a second end portion 134 of the first channel configured to receive a portion of the mouthpiece or the mask 142. The first end portion and second end portion include openings configured to receive the conduit and mask, respectively. The channel may have walls that have smooth surfaces so that air and medication may easily move toward the user or provide a path for air and medication to be in fluid communication with the mouthpiece of the mask. The system further includes a second channel 138 disposed on the housing configured to receive a portion of the capsule 108 and a second longitudinal axis 140 defined by the second channel. In one embodiment, the second channel may be circular in shape, however other shapes may be used and are within the spirit and scope of the present invention. The base unit includes an opening 141 of the second channel that receives a portion of the capsule. The second longitudinal axis defines at most a 90-degree angle relative to the first longitudinal axis of the first channel. In the present embodiment, the angle 143 between the second longitudinal axis and first longitudinal axis is at a 45 degree angle. However, other angles that allow the medication to easily flow into the second channel may be used and are within the spirit and scope of the present invention.

The fresh air then moves through tubular chamber in direction B while the atomized medication moves through base unit in direction C such that the fresh air and the medication atomized by the atomizer mix together within the tubular chamber to create a mixture 170. The system further includes a mask 142 defining a mask chamber 144 within the mask. The mask is configured to be positioned over the patient's mouth and nose. The mask has a rim 146 extending about a periphery of the mask for forming a seal with the patient's face and a mouthpiece defining a tubular shaped body. The mixture 170 of the fresh air and the atomized medication flows towards the mask in direction D.

The system further includes a processor 148 housed by the housing of the base unit. Two electrical contacts 152 are positioned within the second channel. The capsule also includes two electrical contacts (shown in FIG. 2) that mate with the two electrical contacts within the second channel providing electrical communication with the power source 154 of the base unit. The power source may be a battery power source. In the present embodiment, the battery power source may be a battery power source, such as a standard dry cell battery commonly used in low-drain portable electronic devices (i.e., AAA batteries, AA batteries, etc.). Other types of batteries may be used including rechargeable batteries, aluminum air batteries, lithium batteries, paper batteries, lithium-ion polymer batteries, lithium iron phosphate batteries, magnesium iron batteries etc. Additionally, other types of battery applications may be used and are within the spirit and scope of the present invention. For example, a battery stripper pack may also be used. Additionally, other types of power sources may also be used and are within the spirit and scope of the present invention. In other embodiments, the power source may be an external power source. For example, the system may include a power cable that can connect to an electrical wall outlet. Other types of external power sources may be used and are within the spirit and scope of the present invention.

The base unit may also include a sensor 156 that detects whether a capsule is inserted into the second channel or not. The housing also houses a user interface 150. The user interface is configured to be acted on by a rescuer to start the atomizer to atomize the medication. The user interface may include controls to set or adjust the rate of medication to administer, to start or stop the atomizer, and/or to gain authorization to the base unit. The user interface may also include a graphical display configured to receive gestures such as touches, swipes, etc. to control the device. The user interface may also be controlled by receiving sound commands that are received by an audio sensor and then processed by the processor. The processor is configured for receiving a signal to start the atomizer to atomize the medication, sending a second signal to the atomizer to cause the atomizer to atomize the medication within the capsule and convey the atomized medication into the second channel, receiving a third signal from the sensor when the sensor detects that the medication within the capsule is less than a minimum threshold, and sending a fourth signal to turn off the atomizer after the third signal is received. For example, the minimum threshold may be an amount of fluid that is left in the container is less than 1/12 the total of medication in the capsule. For example, the sensor may detect that minimum threshold amount of medication is within the capsule, send the signal to the processer, then the processer may send a signal to stop the atomizer.

In some embodiments, the system may include a storage case such as, but not limited to, a briefcase. The storage may be able to hold multiple attachments, or base unit(s) 106, that can be charged by a power source within the storage case. The briefcase may require security measures to be unlocked. For example, unique codes or a fingerprint scanner may be used as a security measure. The storage case may include slots to hold a capsule that may be prefilled or non-prefilled with medication. The storage case would be very useful in medical emergencies.

Referring now to FIG. 2, a side view of a system 200 for administering medication to a patient is shown, according to a second embodiment. Instead of the mask in the first embodiment, the second embodiment of the system for administering medication to a patient includes a mouthpiece 205. In one embodiment, the mouthpiece may be a tubular shaped body that is shaped to be inserted into a patient's mouth so that the user may inhale atomized medication into the patient's mouth.

The system 200 also includes electrical contacts 152 exposed on the inner surface of the second channel 138 that pair with electrical contacts 215 exposed on the outer surface of the capsule. When electrical contacts 152 and 215 are touching each other, the sensor 156 sends a signal to the processor 148, which sends a signal to turn on the power source 154. The power source then provides electrical power to the capsule 108 such that the atomizer begins atomizing the medication if there is electrical communication between contacts 152 and 215. The main difference between the first embodiment and the second embodiment is that they have different medical components (mask vs. mouthpiece) in attachment with the receiving sections 107 and 109 of the base unit. The system also includes an interface 150 on the second side of the base unit and is configured to allow the user to send signals to the processor to control the atomizer. The second embodiment allows a rescuer, medical professional, or in certain cases the patient to use the system on a patient that is positioned upright and is conscious, unlike the first embodiment, wherein the patient is laying down and may be unconscious. Upright means that the patient's body is substantially vertical so the patient's head 160 is substantially vertical.

Referring now to FIGS. 3A through 3D, 11A, 11B, and 12, various views of a third embodiment of the system for administering medication to a patient are shown. FIG. 3A is a diagram of side view of the base unit 300 of the system for administering medication to a patient, according to the third embodiment. FIG. 3B is a diagram of a side view of the base unit 300 of the system for administering medication to a patient, according to the third embodiment. FIG. 3C is a diagram 301 illustrating the main electrical components of the system for administering medication to a patient, according to the third embodiment. FIG. 3D is a diagram 301 illustrating the main electrical components of the system for administering medication to a patient, according to the third embodiment. Additionally, FIGS. 11A through 12 also depict views of other examples of the third embodiment of the system for administering medication to a patient. FIG. 11A and FIG. 11B are various views of the system having a mouthpiece 1105 in attachment with the base unit 300, according to the third embodiment. FIG. 11A may include a graphical display 311 that is configured to provide visual instructions, warnings, maintenance items to the patient, such as when to start inhaling, when to stop inhaling, battery life of the device etc. when the device is in operation. The system may also include an audio component such as a speaker 314 to provide audio instructions (that are similar to the instructions provided by graphical display 311). The system may also include a sensor 316 for receiving audio commands from a user, such as when to start or stop the atomizer however other type of audio commands may be used and are within the spirit and scope of the present invention. The attachment may also include a cap 319 or cover that covers the opening of the receiving section. The cap may be configured to cover the opening so that when no bag is attached to the receiving section, the device may still be used as an atomizer for atomizing medication.

Figure 3A:
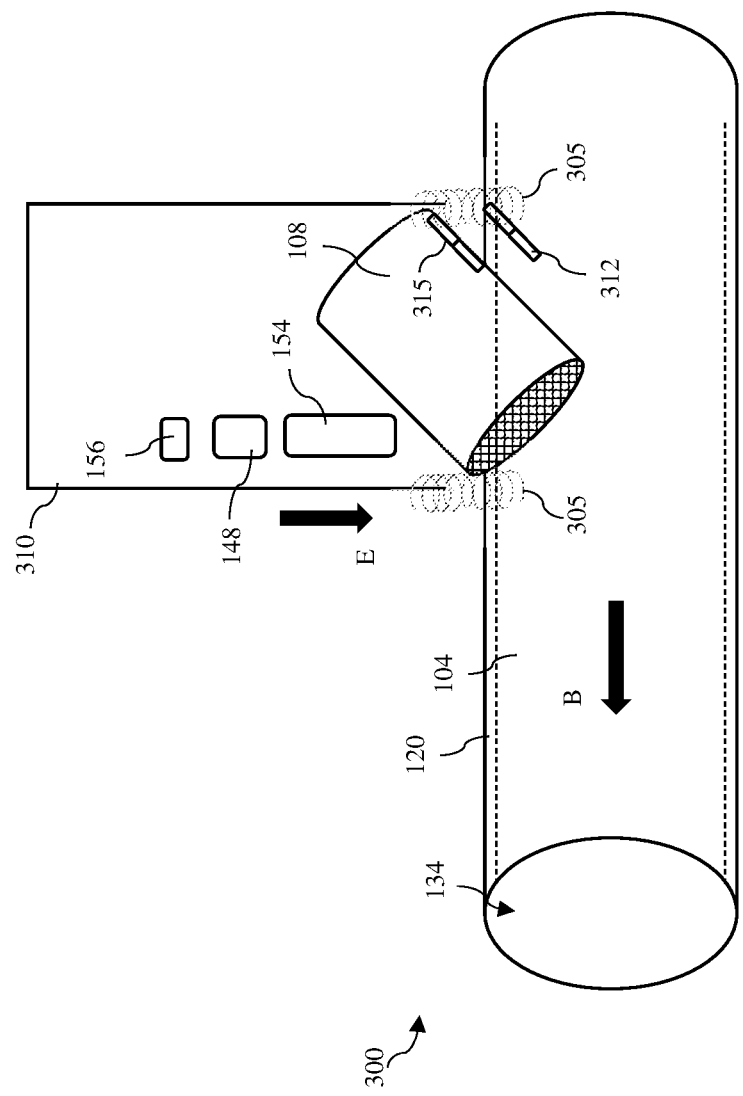
Figure 3B:
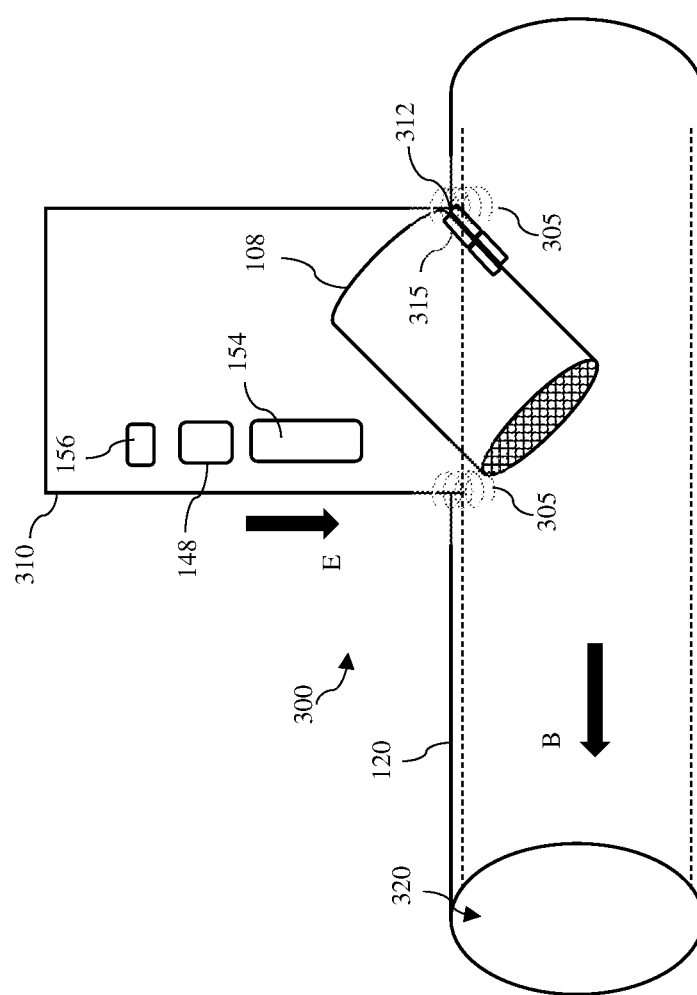

Referring back to FIG. 3A and 3B, the housing includes biasing elements 305 that are positioned between the housing 120 and an engaging element 310 that receives the capsule. In one embodiment, the biasing elements may be compressing springs. However, other biasing elements may be used and are within the spirit and scope of the present invention. The engaging element is a component that a user of the system interacts with to start the atomization of the medication. The engaging element is in attachment with the housing 120 of the base unit. The engaging element is similar to a button such that the user pushes down on the engaging element, which then interacts with the housing of the base unit. The engaging element may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The engaging element may be made of other materials and is within the spirit and the disclosure. The engaging element may be formed from a single piece or from several individual pieces joined or coupled together. The components of the engaging element may be manufactured from a variety of different processes including an extrusion process, a mold, casting, welding, shearing, punching, folding, 3D printing, CNC machining, etc. However, other types of processes may also be used and are within the spirit and scope of the present invention. The engaging element is shaped such that a user of the system can use one hand to push down on the engaging element. The third embodiment is convenient because it allows the user to self-administer medication.

A patient can push down or apply a force on the engaging element in direction E such that the engaging element moves towards the housing. When force in of line E is applied to overcome the expansion force of the spring, the engaging element 310 moves toward the housing to a certain extent so that the electrical contacts 312 of the housing and the electrical contacts 315 of the capsule contact each other to provide electrical communication between the power source and the atomizer in the capsule. The patient must provide enough force downward to hold down to allow the electrical contacts to remain in contact such that the atomizer continues to atomize the medication in the capsule. This causes the medication to be dispensed into the tubular chamber 104 for as long as electrical contacts of the housing are in contact with the electrical contacts of the capsule. The atomized medication then moves in direction B towards the end portion 320 of the base unit where a mouthpiece or mask may be attached to. The end portion 320 is similar to the first end portion 130 and the second end portion 134 such that it includes a receiving section with modular fittings. Referring back to FIG. 11B, the user may view the graphical display 311, which may provide instructions as to how long to apply force to cause the medication to be atomized by the device.

FIG. 12 is a perspective view of system having a mask 1110 in attachment with the base unit 300, according to the third embodiment. Shown in FIG. 11A and 11B, a mouthpiece 1105 is in attachment with the end portion 320. In FIG. 12, a mask is in attachment with the end portion 320. The third embodiment can be easily used by one person as opposed to the first embodiment and second embodiment because only one hand is needed. A conscious patient can perform treatment on his or herself when using the third embodiment. The capsule may also include a sensor 535, also shown in FIG. 5, that detects the amount of medication remaining in the capsule.

Referring now to FIG. 5, a front view of a capsule 500 is shown, according to an example embodiment. Additionally, with reference to FIG. 16A and FIG. 16B, various views of the capsule 1600 are shown, according to an example embodiment. The capsule includes a capsule chamber 505 for housing the medication 510 and a rubber section 515 covering an open side 520 of the capsule. In the present embodiment, the capsule chamber can hold up to 20 milliliters of fluid. In other embodiments, the capsule chamber may hold other volumes of fluid, which is within the spirit and scope of the present invention. The rubber section allows for medication to be inserted into the capsule. A user of the capsule may add medication by inserting a syringe through the rubber section and using the syringe to dispense the medication into the capsule chamber 505. The capsule further includes the atomizer 525 proximate to a second side 530 of the capsule and a sensor 535 for detecting the amount of the medication in the capsule. In operation, the capsule chamber is above the atomizer and abuts the atomizer such that gravity allows the medication to go through the atomizer. Gravity forces the medication down such that the medication presses down against the atomizer. The sensor 535 may be a float sensor that measures the level of liquid in the capsule chamber. However, other sensors may be used and are within the spirit and scope of the present invention. After all the medication in the capsule chamber is dispensed through the atomizer, a maximum amount of the medication has been dispensed, or the maximum amount of time has passed, sensor 535 sends a signal to the processor to stop the atomizer. The float sensor is a continuous level sensor featuring a magnetic float that rises and falls as liquid levels change. The movement of the magnetic float creates a magnetic field that actuates a hermetically sealed reed switch located in the stem of the level sensor, triggering the switch to open or close. Other types of sensors configured to detect the amount of liquid in the capsule chamber may be used and are within the spirit and scope of the present invention. Additonally, the maximum amount of medication or time may be adjusted depending on the patient, medication and variety of other factors.

The capsule may also include a removeable covering 550, such as, but not limited to, a cap or seal, in attachment with the second side 530 of the capsule to preserve the medication and/or prevent the medication from leaking. The removeable covering allows users of the system to store capsules for emergency use or long-term use, depending on the type of removeable covering. In some embodiments, the capsule may be color-coded for emergency medication or may include labels that identify the medication within the capsule. The capsule may also include a locking element that prevents the capsule from atomizing the medication unless an access code is provided. The access code may be provided via the remote computing device (708 in FIG. 7) and may be a biometric element or an alphanumeric element.

The capsule may also include a processor 540 and a power source 545. In some embodiments, the method for atomizing the medication described herein may be performed by the processor 540 of the capsule. The power source may be a battery power source. In the present embodiment, the battery power source may be a battery power source, such as a standard dry cell battery commonly used in low-drain portable electronic devices (i.e., AAA batteries, AA batteries, etc.). Other types of batteries may be used including rechargeable batteries, aluminum air batteries, lithium batteries, paper batteries, lithium-ion polymer batteries, lithium iron phosphate batteries, magnesium iron batteries etc. Additionally, other types of battery applications may be used and are within the spirit and scope of the present invention. For example, a battery stripper pack may also be used. Additionally, other types of power sources may also be used and are within the spirit and scope of the present invention. In other embodiments, the power source may be an external power source. For example, the system may include a power cable that can connect to an electrical wall outlet. Other types of external power sources may be used and are within the spirit and scope of the present invention. The capsule may also include electrical contacts 1605 that pair with the electrical contacts in the second channel of the base unit.

Figure 4:
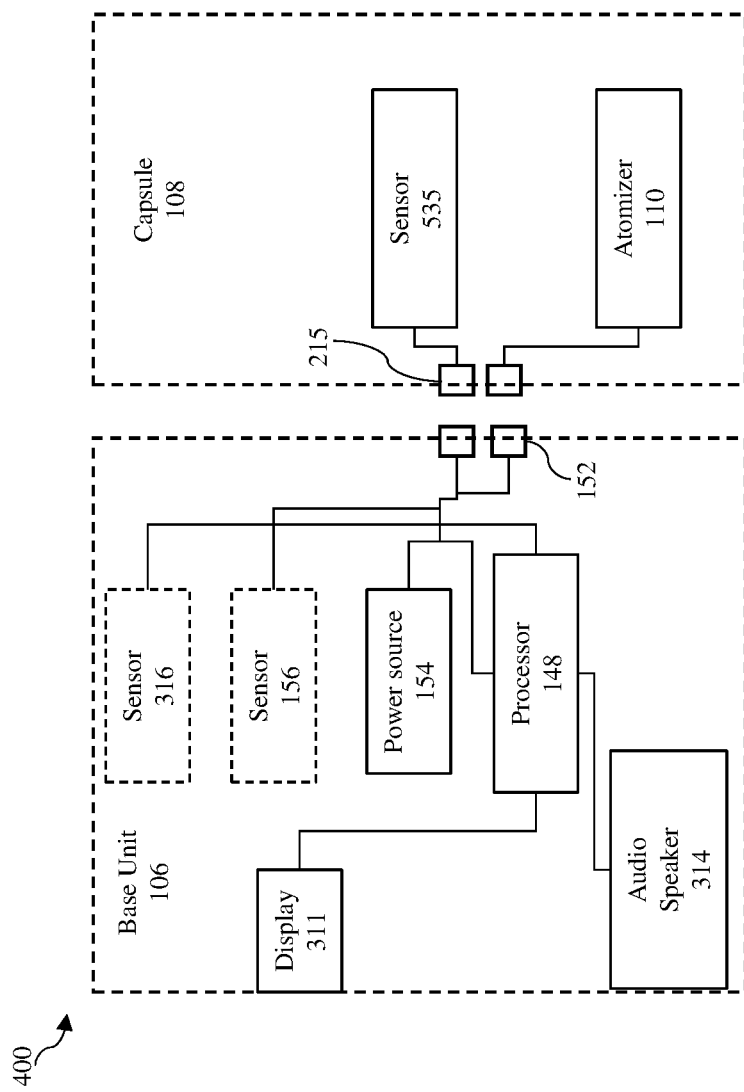

Referring now to FIG. 4, a diagram 400 illustrating the main electrical components of the system for administering medication to a patient is shown, according to an example embodiment. Within the base unit 106, the sensor 156, the power source 154, the processor 148, and a pair of electrical contacts 152 are in electrical communication with each other. Additionally, within the capsule 108, the atomizer 110, the sensor 535, and a pair of electrical connectors 215 are in electrical communication with each other. When the two pairs of electrical contacts are contacting each other, the system provides electrical communication between the base unit and the capsule, such that the power source can power the atomizer when the processor of the base unit receives the signal to start the atomizer.

Figure 6B:
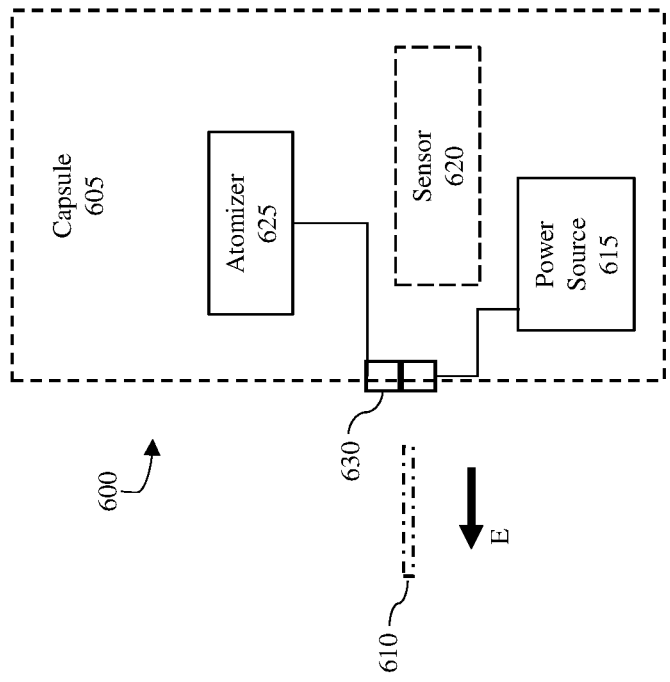
FIG. 6B is a diagram illustrating the main electrical components of the capsule, wherein an electrical insulator in form of a tab is removed from between two contacts, according to an example embodiment.
Figure 6A:
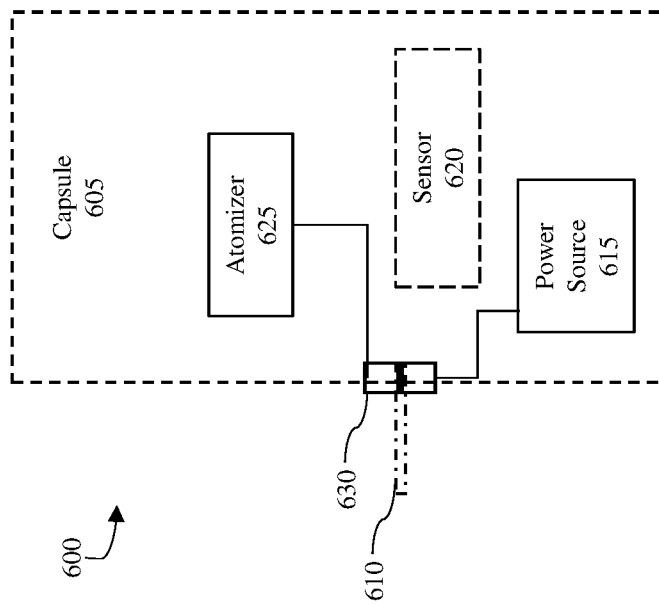
FIG. 6A is a diagram illustrating the main electrical components of the capsule, wherein an electrical insulator in form of a tab is positioned between two contacts, according to an example embodiment.

Referring now to FIG. 6A and FIG. 6B, a diagram 600 illustrating the main electrical components of the capsule 605 with an electrical insulator in the form of a tab 610 is shown, according to an example embodiment. In this embodiment, the capsule includes a power source 615, a sensor 620, and the atomizer 625 in electrical communication. The power source 615 is the same as the power source 545 described with reference to FIG. 5. The capsule also includes at least two contacts 630 that can provide electrical communication between the power source and the atomizer. In FIG. 6A, the electrical contacts are separated by a tab that blocks the electrical communication between the power source and the atomizer. The tab may be comprised of material including rubber, synthetic rubber, like latex or silicone, and plastics such as Polyvinyl Chloride, Teflon (PTFE—Polytetrafluoroethylene), and Polyethylene. However, other materials configured to insulate electricity may be used and are within the spirit and scope of the present invention. They offer excellent resistance to electricity, and their physical properties can be adjusted to suit specific applications.

When a user of the capsule pulls the tab out from between the electrical contacts, the electrical contacts can contact each other and provide electrical communication between the power source and the atomizer. In this embodiment, the amount of energy within the power source is configured to run out after all of the medication within the capsule is atomized. This is useful for medical emergencies because the rescuer can quickly pull out the tab and quickly insert the capsule into the base unit.

Figure 7:
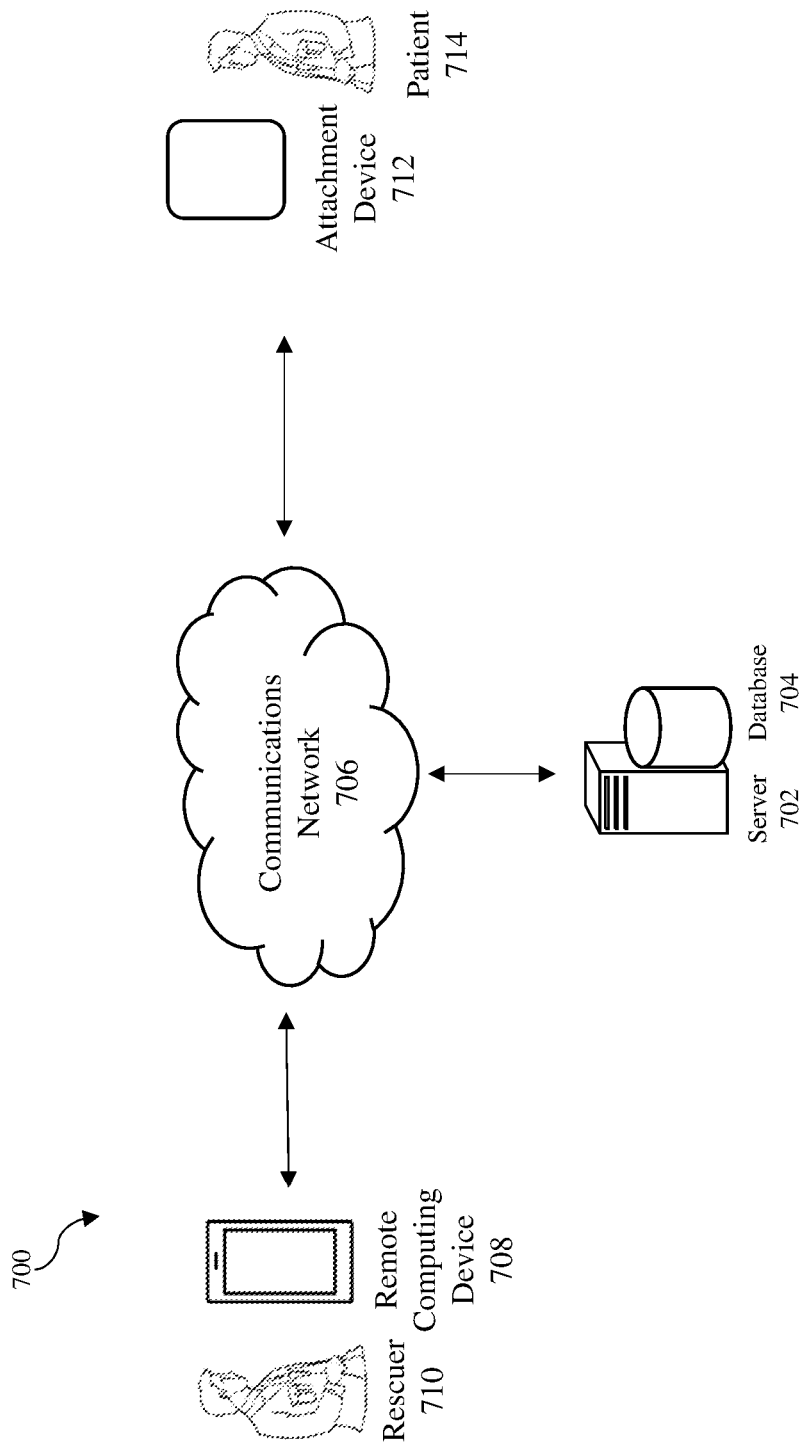
FIG. 7 is a diagram of an operating environment that supports a system of administering medication to a patient, according to an example embodiment.

Referring now to FIG. 7. is a diagram of an operating environment 700 that supports a system of administering medication to a patient is shown, according to an example embodiment. FIG. 7 is a diagram of an operating environment that supports a system of administering medication to a patient, according to an example embodiment. The most prominent element of FIG. 7 is the server 702 associated with repository or database 704 and further coupled with the communications network 706, which can be a circuit switched network, such as the Public Service Telephone Network (PSTN), or a packet switched network, such as the Internet or the World Wide Web, the global telephone network, a cellular network, a mobile communications network, or a Personal Area Network (PAN), such as Bluetooth® or any combination of the above. In one embodiment, network 706 is a secure network wherein communications between endpoints are encrypted so as to ensure the security of the data being transmitted. Server 702 is a central controller or operator for the functionality that executes on at least a remote computing device 708 and an attachment device 712, via various methods.

FIG. 7 further includes the remote computing device 708 and the attachment device 712, which are computing devices that each may be smart phones, mobile phones, tablet computers, handheld computers, laptops, or the like. The remote computing device corresponds to a rescuer 710, and the attachment device 712 corresponds to the attachment, or base unit (106 in FIG. 1), that is associated with the cardiopulmonary device positioned on the face of the patient 714. The remote computing device and attachment device may include transceivers for communicating over the network 706. Each of the computing devices includes a user interface and/or graphical user interface. In certain embodiments, the system may communicate between the remote computing device and the attachment device, over the communications network, where the rescuer is a person who is providing aid to a patient, and the patient is a person needing medical attention. The users of the system input selections via a user interface on the remote computing device to be sent through the communications network via a data packet and to the attachment device.

FIG. 7 further shows that server 702 includes a database or repository 704, which may be one or more of a relational databases comprising a Structured Query Language (SQL) database stored in a SQL server, a columnar database, a document database and a graph database. Computing devices 708 and 712 may also each include their own database. The repository 704 serves data from a database, which is a repository for data used by server 702 and the remote computing device during the course of operation of the invention. Database 704 may be distributed over one or more nodes or locations that are connected via network 706.

FIG. 7 shows an embodiment wherein networked computing devices 708 and 712 may interact with server 702 and repository 704 over the network 706. Server 702 includes a software engine that delivers applications, data, program code and other information to networked computing devices 708 and 712. The software engine of server 702 may perform other processes such as audio and/or video streaming or other standards for transferring multimedia data in a stream of packets that are interpreted and rendered by a software application as the packets arrive. It should be noted that although FIG. 7 shows only two networked mobile computing devices 708 and 712, the system of the present invention supports any number of networked mobile computing devices connected via network 706, having at least the remote computing device 708 and the attachment device 712.

Server 702 also includes program logic comprising computer source code, scripting language code or interpreted language code that is compiled to produce executable file or computer instructions that perform various functions of the present invention. In another embodiment, the program logic may be distributed among more than one of server 702, computing devices 708 and 712, or any combination of the above.

Note that although server 702 is shown as a single and independent entity, in one embodiment of the present invention, the functions of server 702 may be integrated with another entity, such as each of computing devices 708 and 712. Further, server 702 and its functionality, according to a preferred embodiment of the present invention, can be realized in a centralized fashion in one computer system or in a distributed fashion wherein different elements are spread across several interconnected computer systems.

Figure 8:
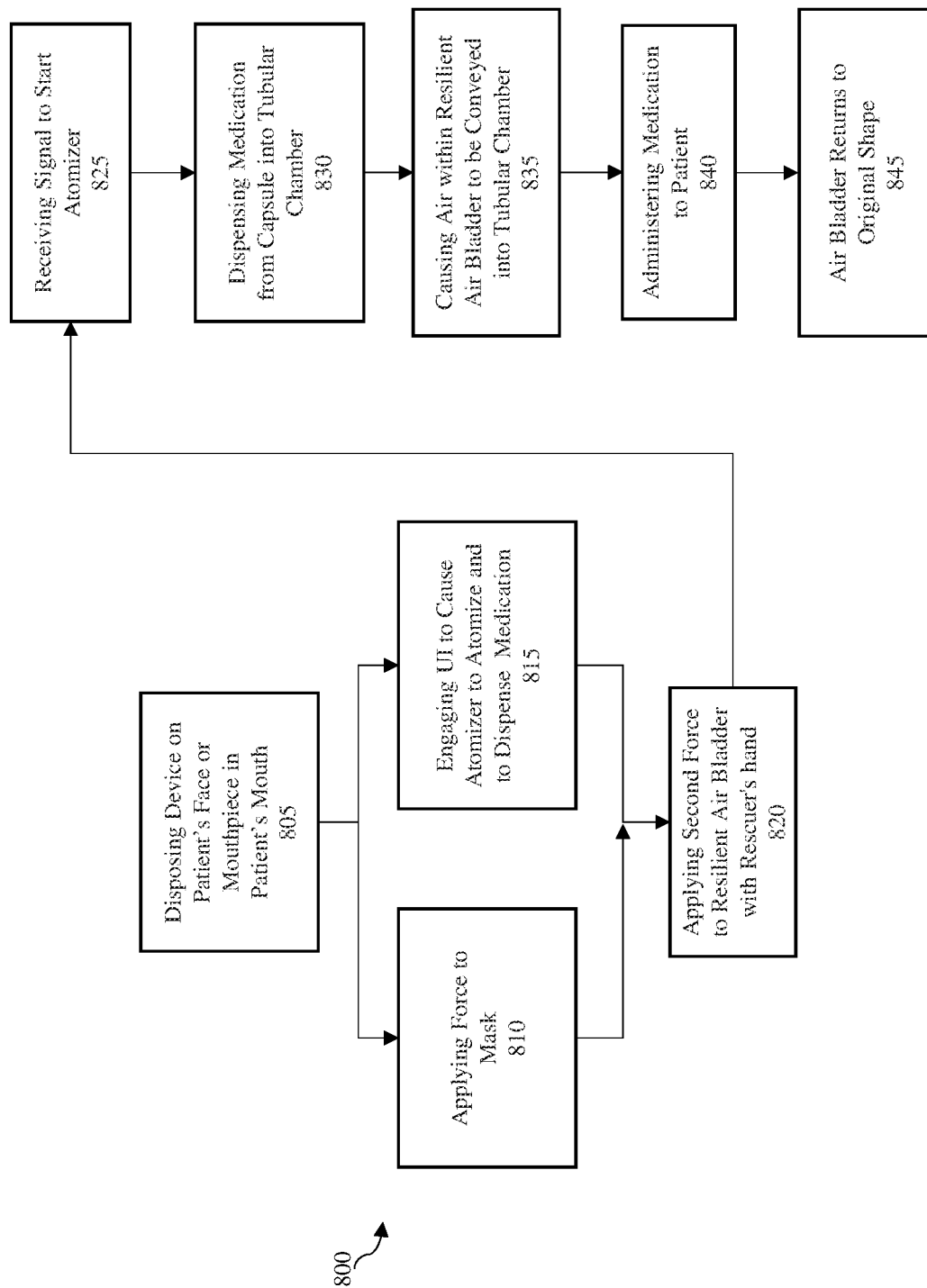
FIG. 8 is a flowchart diagram illustrating steps for a method of administering medication to a patient, according to an example embodiment.

The process of administering medication to the patient will now be described with reference to FIG. 8 and FIG. 1A. FIG. 8 is a flowchart diagram illustrating steps for a method 800 of administering medication to a patient, according to an example embodiment. FIG. 1A is a diagram of the system 100 showing the patient's head 160 and the hands of the rescuer. In step 805, prior to dispensing the medication from the capsule, the rescuer disposes the mask of the device over the patient's mouth and nose and/or a mouthpiece to be inserted into the patient's mouth. In step 810, the rescuer uses a hand to apply a force to the mask to obtain a substantially air-tight seal against the patient's face. The substantially air-tight seal is created because the rim 146 surrounds the nose and mouth of the patient and is pressed against the patient's face. Shown in FIG. 1A, the rescuer, uses a hand 162 to apply a force in direction F to hold the mask 142 over the patient's face. The force in the direction of F causes the substantially airtight seal. It is understood that the substantially airtight seal needs to allow most of the medication to be administered to a patient's face. In step 815, while applying the force with the hand to the mask, the rescuer engages, with a second hand (164 in FIG. 1A) of the rescuer, the user interface 150 on the device to cause the atomizer to atomize the medication (510 in FIG. 5) and to dispense the atomized medication 166 from the capsule. In step 820, while applying the force to the mask with the hand of the rescuer and either during or after engaging the user interface to cause the dispensing of the medication from the capsule, the rescuer applies a second force with the second hand 164 of the rescuer, to the resilient air bladder 102 so that the fresh air 168 within the resilient air bladder is conveyed via the conduit 132 from the resilient air bladder 102 and into the tubular chamber 104 such that the air conveyed from the resilient air bladder and the medication dispensed from the capsule is administered to the patient. In step 825, prior to dispensing the medication from the capsule, the system receives, with a processor, a signal to start the atomizer 110 to atomize the medication. In step 830, the system dispenses, using the atomizer, the medication from the capsule in fluid communication with the tubular chamber, into the tubular chamber. As mentioned above, the maximum amount of medication or amount of time the medication is atomized may be adjusted based on a variety of factors. The angle between the longitudinal axis of the second channel and the longitudinal axis of the first channel may be approximately 45 degrees so that the atomized medication can easily move and combine with air within the first channel.

In step 835, the system causes fresh air 168 within a resilient air bladder in fluid communication with the tubular chamber to be conveyed from the resilient air bladder 102 through the conduit 132. The fresh air then flows into the tubular chamber to mix with the atomized medication. In step 840, the air conveyed from the resilient air bladder and the medication dispensed from the capsule is administered to the patient. In step 845, the resilient air bladder 102 returns to its original shape such that the rescuer may squeeze it again to supply more fresh air into the system.

It is understood that this method is a continuous cycle and that each step of method 800 may operate concurrently with another step of method 800 to provide efficient administration of medication within the system. In other embodiments, the method may further include additional steps to promote efficient administration of medication consistent with the systems disclosed herein.

Figure 9:
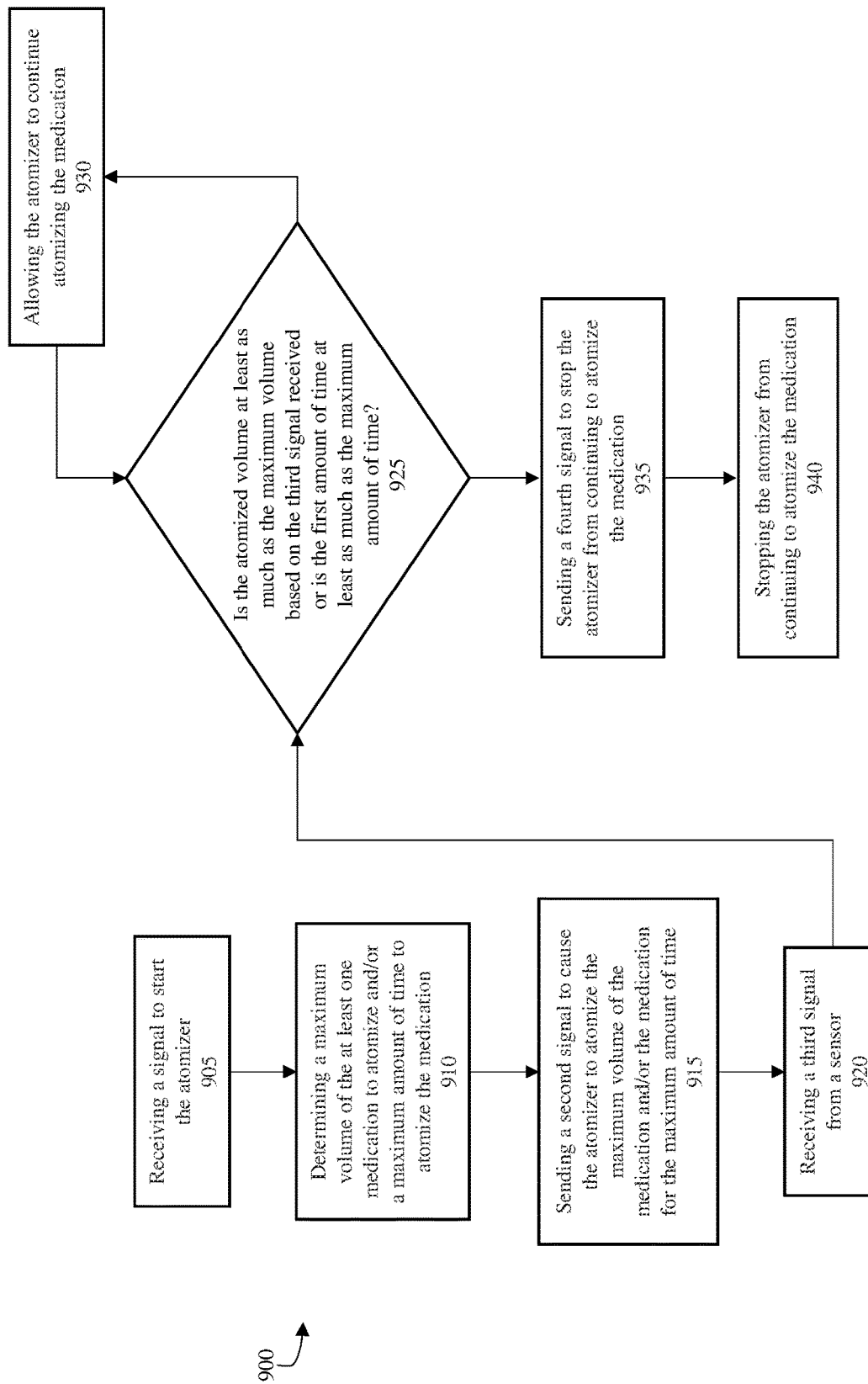
FIG. 9 is a flowchart diagram illustrating steps for a method of atomizing medication, according to an example embodiment.
Figure 10:
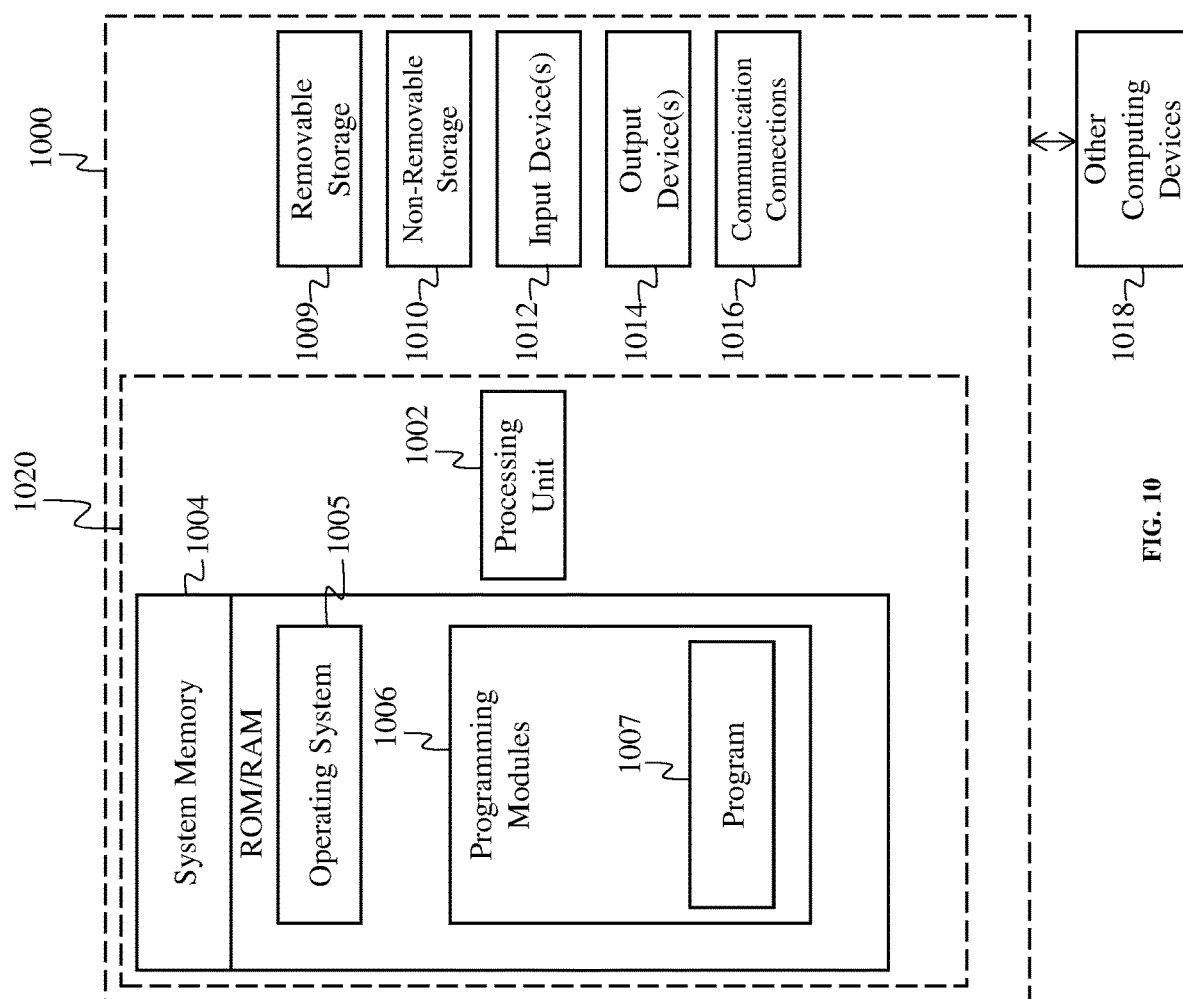
FIG. 10 is a block diagram of a system including a computing device and other computing devices, according to an exemplary embodiment of present technology.
Figure 11B:
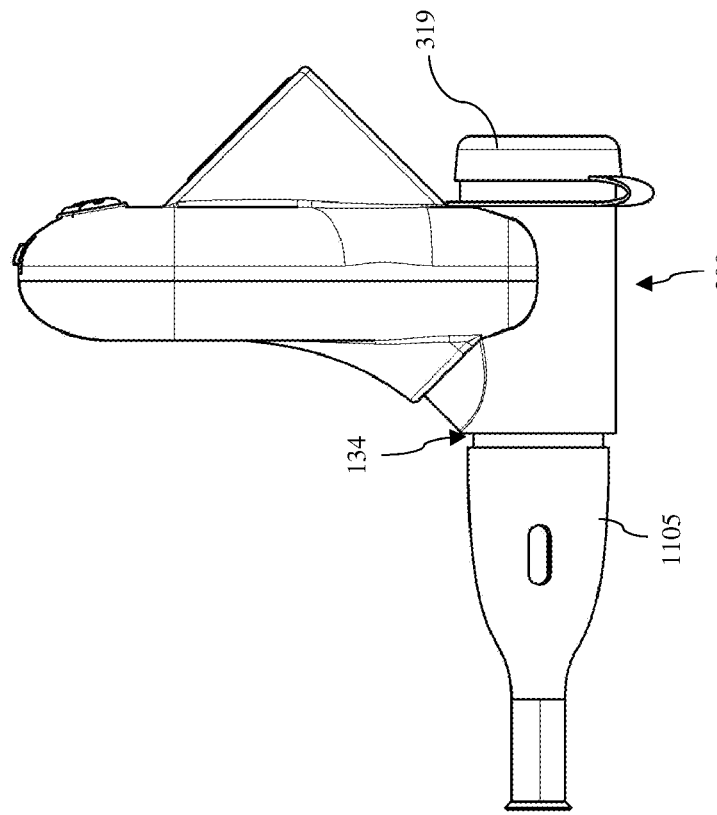
FIG. 11B is a side view of a system for administering medication to a patient, according to the third embodiment.
Figure 11A:
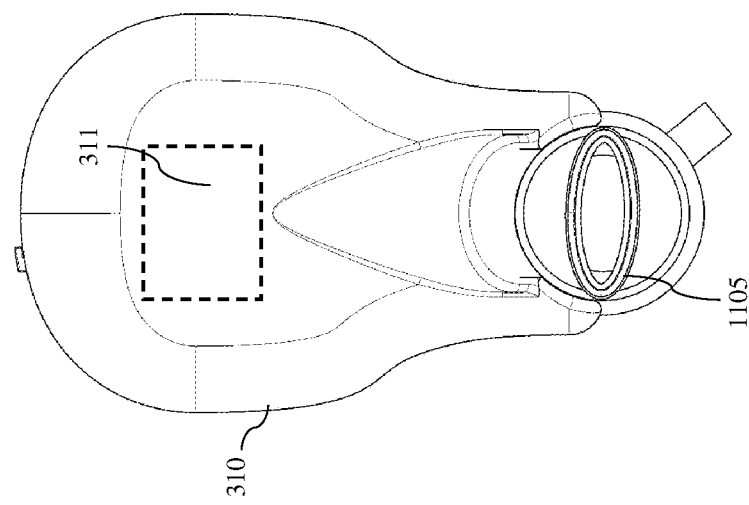
FIG. 11A is a front view of a system for administering medication to a patient, according to the third embodiment.
Figure 12:
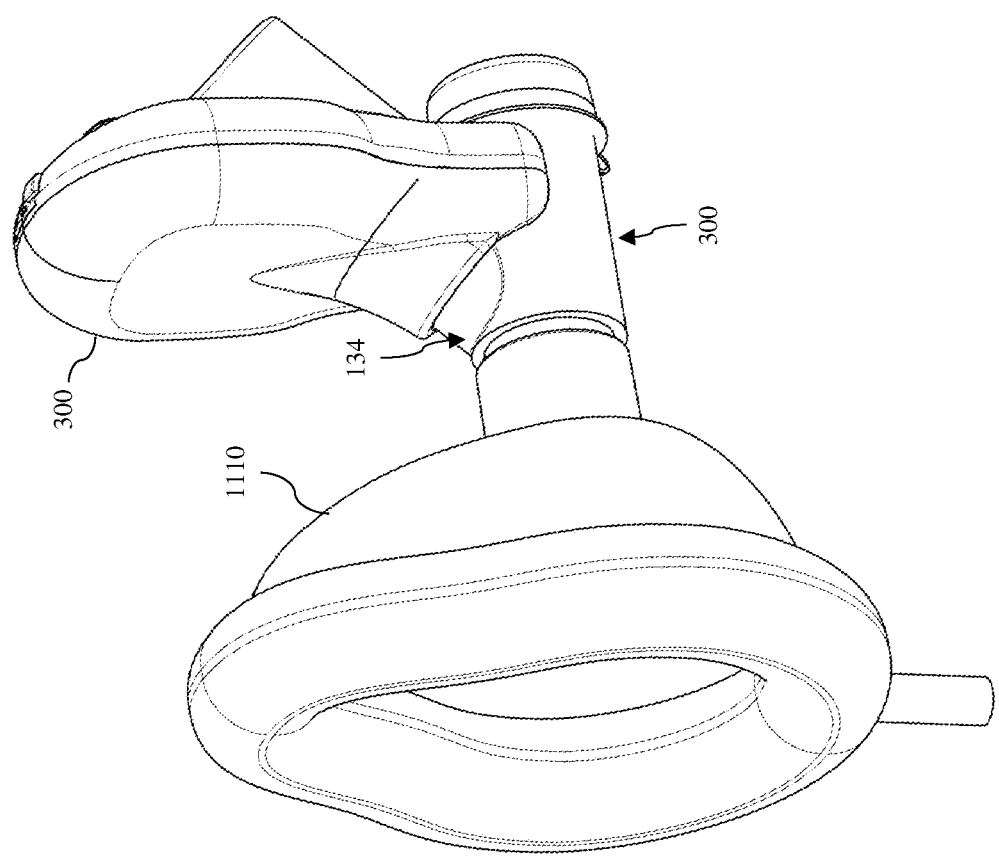
FIG. 12 is a perspective view of a system for administering medication to a patient, according to the third embodiment.

With reference to FIG. 7 and FIG. 9, the process of atomizing the medication will be described. FIG. 9 is a flowchart diagram illustrating steps for a method 900 of atomizing medication, according to an example embodiment. The method 900 is performed by the processor of the attachment device. In step 905, the attachment device 712 receives a signal to start the atomizer to atomize the medication. The signal is received from the remote computing device. The signal may include data that allows the processor within the attachment device to determine that the atomizer should start to atomize medication within the capsule. Additionally, the data may include information to set the atomizer to atomize for a certain amount of time (for example a minimum or maximum) or certain amount of fluid (for example a minimum or maximum). This allows the rescuer or medical professional to control the dosage of the medication to the patient. The attachment device 712 may communicate with the remote computing device via Bluetooth®. The attachment device 712 may include security measures, such as requiring the rescuer to input unique identifier, such as a security code or biometric information (such as a fingerprint) via the remote computing device to send the signal. For example, the rescuer may be a medical professional that is assigned a Personal Identification Number ("PIN") that, when entered into the remote computing device, allow the remote computing device to send the signal to start the atomizer within the capsule. Other examples of security codes may include, but are not limited to, a one-time-password, two-factor authentication codes, activation codes, or access codes. Other types of security measures configured to prevent unauthorized usage of the system may be used and are within the spirit and scope of the present invention.

In step 910, the attachment device determines, based on the signal, a maximum volume of the medication to atomize or a maximum amount of time to atomize the medication. The maximum amount of time can be set to a certain amount of time and can be adjusted during operation. For example, the maximum amount of time may be 2-10 seconds, 1 minute, etc. The maximum volume can be set to a certain volume and adjusted during operation. For example, the maximum volume may be 1, 2 or 4 milliliters. However, other embodiments may be used and are within the spirit and scope of the present invention. In step 915, the attachment device sends, to the atomizer, a second signal to cause the atomizer to atomize the maximum volume of the medication and/or the medication for the maximum amount of time. The maximum volume and the maximum amount of time depends on the signal sent by the remote computing device. In step 920, the attachment receives, from the atomizer, a third signal from the sensor that monitors an atomized volume of the medication within the capsule and/or a first amount of time the atomizer atomizes the medication. In step 925, the processor of the attachment device determines if the atomized volume is at least as much as the maximum volume based on the third signal received and/or the first amount of time is least as much as the maximum amount of time. In step 930, if the attachment device determines the atomized volume is not at least as much as the maximum volume based on the third signal received and/or the first amount of time is not at least as much as the maximum amount of time, the attachment device allows the atomizer to continue atomizing the medication. In step 935, after the attachment device determines the atomized volume is at least as much as the maximum volume based on the third signal received and/or the first amount of time is least as much as the maximum amount of time, the attachment device sends a fourth signal to stop the atomizer from continuing to atomize the medication within the capsule. In step 940, the attachment device stops the atomizer from continuing to atomize the medication within the capsule.

It is understood that this method is a continuous cycle and that each step of method 900 may operate concurrently with another step of method 900 to provide efficient atomization of medication within the system. In other embodiments, the method may further include additional steps to promote efficient atomization of medication consistent with the systems disclosed herein. In some embodiments, the steps of method 900 may be performed by a processor within the capsule.

Referring now to FIG. 10, a block diagram of a system including an example computing device 1000 and other computing devices is shown, according to an exemplary embodiment of present technology. Consistent with the embodiments described herein, the aforementioned actions performed by devices 708 and 712 may be implemented in a computing device, such as the computing device 1000 of FIG. 10. Any suitable combination of hardware, software, or firmware may be used to implement the computing device 1000. The aforementioned system, device, and processors are examples and other systems, devices, and processors may include the aforementioned computing device. Furthermore, computing device 1000 may include an operating environment for systems 100 and processes 800, 900 and others described herein. Processes 800, 900 and others described herein may operate in other environments and are not limited to computing device 1000.

With reference to FIG. 10, a system consistent with an embodiment of the invention may include a plurality of computing devices, such as computing device 1000. In a basic configuration, computing device 1000 may include at least one processing unit 1002 and a system memory 1004. Depending on the configuration and type of computing device, system memory 1004 may include, but is not limited to, volatile (e.g., random access memory (RAM)), non-volatile (e.g., read-only memory (ROM)), flash memory, or any combination or memory. System memory 1004 may include operating system 1005, and one or more programming modules 1006. Operating system 1005, for example, may be suitable for controlling computing device 1000's operation. In one embodiment, programming modules 1006 may include, for example, a program module 1007 for executing the actions of devices 708 and 712, for example. Furthermore, embodiments of the invention may be practiced in conjunction with a graphics library, other operating systems, or any other application program and is not limited to any particular application or system. This basic configuration is illustrated in FIG. 10 by those components within a dashed line 1020.

Computing device 1000 may have additional features or functionality. For example, computing device 1000 may also include additional data storage devices (removable and/or non-removable) such as, for example, magnetic disks, optical disks, or tape. Such additional storage is illustrated in FIG. 10 by a removable storage 1009 and a non-removable storage 1010. Computer storage media may include volatile and nonvolatile, removable and non-removable media implemented in any method or technology for storage of information, such as computer readable instructions, data structures, program modules, or other data. System memory 1004, removable storage 1009, and non-removable storage 1010 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 1000. Any such computer storage media may be part of device 1000. Computing device 1000 may also have input device(s) 1012 such as a keyboard, a mouse, a pen, a sound input device, a camera, a touch input device, microphone for capturing audio sound (which may include commands to operate the device). Output device(s) 1014 such as a display, speakers, a printer, etc. may also be included. The aforementioned devices are only examples, and other devices may be added or substituted.

Computing device 1000 may also contain a communication connection 1016 that may allow device 1000 to communicate with other computing devices 1018, such as over a network in a distributed computing environment, for example, an intranet or the Internet. Communication connection 1016 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 1004, including operating system 1005. While executing on processing unit 1002, programming modules 1006 (e.g., program module 1007) may perform processes including, for example, one or more of the stages of the methods 800, 900 as described above. The aforementioned processes are examples, and processing unit 1002 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. It is understood that, in certain embodiments, the functions/acts noted in the blocks may occur out of order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A method of administering at least one medication into a mouth of a patient comprising:
providing a removable capsule having an upper part of a vibrating mesh atomizer disposed at a lower end of and directly adjacent to a capsule chamber of the removable capsule, wherein the at least one medication contacts the upper part of the atomizer within the chamber;
inserting the removable capsule into a channel of a base unit, the channel in fluid communication with a chamber of the base unit, the base unit having a housing that defines openings for receiving a portion of a conduit of a resilient air bladder, a portion of at least one of a mouthpiece and a mask, and the removable capsule, wherein a first electrical contact is disposed on an outward surface of the removable capsule and a second electrical contact is disposed on an inner wall of the channel for providing electrical communication between the removable capsule and the base unit;

dispensing, using the atomizer, by interacting with an interface on the base unit, the at least one medication from the removable capsule to the chamber of the base unit, via the capsule chamber; and causing air within the resilient air bladder in fluid communication with the chamber of the base unit to be conveyed from the resilient air bladder and into the mixing chamber such that the air conveyed from the resilient air bladder and the at least one medication dispensed from the removable capsule is administered to the patient.

2. The method of claim 1 further comprising, prior to dispensing the at least one medication from the removable capsule disposing at least one of a device on a face of the patient, the device comprising the mask defining a mask chamber within the mask, the mask to be positioned over the patient's mouth and nose, and applying force to the mask to obtain a substantially air-tight seal against the patient's face; and the mouthpiece defining a tubular shaped body into the patient's mouth.

3. the method of claim 1 further comprising, while applying a force to the mask, and at least one of during and after engaging with the interface to cause the dispensing of the at least one medication from the removable capsule, applying a second force, to the resilient air bladder, so that the air within the resilient air bladder is conveyed from the resilient air bladder and into the chamber of the base unit such that the air conveyed from the resilient air bladder and the at least one medication dispensed from the removable capsule is administered to the patient.

4. The method of claim 3, prior to dispensing the at least one medication from the removable capsule, further comprising:
a. receiving, with a processor, a first signal to start the atomizer to atomize the at least one medication;
b. determining, using the processor based on the first signal, at least one of (i) a maximum volume of the at least one medication to atomize (ii) and a maximum amount of time to atomize the at least one medication;

c. sending, to the atomizer, a second signal to cause the atomizer to atomize at least one of (i) the maximum volume of the at least one medication and ii) the at least one medication for the maximum amount of time; and d. receiving, from the atomizer, a third signal from a sensor that monitors at least one of (i) an atomized volume of the at least one medication within the removable capsule and (ii) a first amount of time the atomizer atomizes the at least one medication.

5. The method of claim 4, wherein the first signal is received from at least one of a remote computing device and the removable capsule.

6. The method of claim 5, wherein, after the processor determines that at least one of (i) the atomized volume is at least as much as the maximum volume based on the third signal received (ii) and the first amount of time is at least as much as the maximum amount of time, then stopping the atomizer from continuing to atomize the at least one medication within the removable capsule.

7. The method of claim 6, wherein the processor sends a fourth signal to stop the atomizer from continuing to atomize the at least one medication within the removable capsule after the processor determines that the atomized volume is at least as much as the maximum volume based on the third signal received.

8. The method of claim 7, wherein prior to dispensing, using the atomizer, the at least one medication from the removable capsule, the method further comprises causing the first electrical contact to come into electrical communication with the second electrical contact.

9. The method of claim 8, wherein causing the first electrical contact to come into electrical communication with the second electrical contact comprises inserting the removable capsule into the channel of the base unit.

10. The method of claim 8, wherein the channel of the base unit has a first longitudinal axis, and the chamber of the base unit has a second longitudinal axis; and wherein an angle between the second longitudinal axis and the first longitudinal axis is at most 90 degrees.

11. The method of claim 1, wherein prior to dispensing, using the atomizer, the at least one medication from the removable capsule, the method further comprises causing the first electrical contact to come into electrical communication with the second electrical contact.

12. The method of claim 11, wherein causing the first electrical contact to come into electrical communication with the second electrical contact comprises inserting the removable capsule into the channel of the base unit.

13. The method of claim 1, wherein the base unit housing defines at least two receiving sections and the channel of the base unit, wherein the channel of the base unit forms an angle with a first side of the housing.

14. The method of claim 1, further including comprising:
removing the resilient air bladder from a first opening of the base unit;
attaching a cap to the first opening thus capping the chamber of the base unit; then administering the at least one atomized medication to the patient by conveying the at least one atomized medication from the capped chamber of the base unit though at least one of (i) the mouthpiece and (ii) the mask.

15. A system for administering at least one medication to a patient comprising:

a removable capsule for dispensing the at least one medicament, the removable capsule having an upper part of a vibrating mesh atomizer disposed at a lower end of and directly adjacent to a capsule chamber of the removable capsule, wherein the at least one medication contacts the upper part of the atomizer within the chamber;

a base unit comprising a first channel, a chamber, and a user interface, the first channel in fluid communication with the chamber, the base unit having a housing that defines openings for receiving a portion of a conduit of a resilient air bladder, a portion of at least one of a mouthpiece and a mask, and the removable capsule, wherein a first electrical contact is disposed on an outward surface of the removable capsule and a second electrical contact is disposed on an inner wall of the first channel for providing electrical communication between the removable capsule and the base unit, wherein the user interface is configured to be acted on to start the atomizer to atomize the at least one medicament; and the resilient air bladder, the resilient air bladder configured to be placed in fluid communication with the chamber of the base unit such that air conveyed from the resilient air bladder and the at least one medication dispensed from the removable capsule is administrable to the patient.

16. The system of claim 15, wherein the system further comprises at least one of:

the mask defining a mask chamber within the mask, the mask to be positioned over a mouth and nose of the patient, a rim extending about a periphery of the mask for forming a seal with the patient's face; and the mouthpiece defining a tubular shaped body.

17. The system of claim 16, wherein the removable capsule comprises:

the capsule chamber for housing the at least one medication;

a rubber section covering an open side of the removable capsule;

the atomizer proximate to a second side of the removable capsule; and a sensor for detecting an amount of the at least one medication in the removable capsule.

18. The system of claim 17, wherein the housing comprises:

the first channel configured to receive a portion of the removable capsule;

a first longitudinal axis defined by the first channel;

a second channel spanning from a first side of the housing to a second side of the housing;

a second longitudinal axis of the second channel;

a first end portion of the second channel configured to receive the portion of the conduit of the resilient air bladder;

a second end portion of the second channel configured to receive the portion of at least one of the mouthpiece and the mask;

the second longitudinal axis defining at most a 90-degree angle relative to the first longitudinal axis; and a processor housed by the housing.

19. The system of claim 18, wherein the processor is configured for:

a. receiving a first signal to start the atomizer;

b. sending a second signal to the atomizer to cause the atomizer to atomize the at least one medication within the capsule and convey the at least one atomized medication into the second channel;

c. receiving a third signal from the sensor when the sensor detects that the at least one medication within the capsule is less than a minimum volume threshold; and d. after the third signal is received, then sending a fourth signal to turn off the atomizer.

* * * * *